US009416367B2

(12) United States Patent
McLaren et al.

(10) Patent No.: US 9,416,367 B2
(45) Date of Patent: Aug. 16, 2016

(54) PLANTS WITH IMPROVED NITROGEN UTILIZATION AND STRESS TOLERANCE

(71) Applicant: Iowa Corn Promotion Board, Johnston, IA (US)

(72) Inventors: James McLaren, Chesterfield, MO (US); Nicholas Duck, Research Triangle Park, NC (US); Brian Vande Berg, Morrisville, NC (US); Alissa Nicole Anthony, Cary, NC (US); Vadim Beilinson, Research Triangle Park, NC (US); Jill Hinson, Research Triangle Park, NC (US)

(73) Assignee: Iowa Corn Promotion Board, Johnston, IA (US)

( * ) Notice: Subject to any disclaimer, the term of this patent is extended or adjusted under 35 U.S.C. 154(b) by 0 days.

(21) Appl. No.: 14/563,536

(22) Filed: Dec. 8, 2014

(65) Prior Publication Data

US 2015/0096077 A1    Apr. 2, 2015

Related U.S. Application Data

(62) Division of application No. 13/309,308, filed on Dec. 1, 2011, now abandoned, which is a division of application No. 11/977,768, filed on Oct. 26, 2007, now abandoned.

(60) Provisional application No. 60/854,927, filed on Oct. 27, 2006.

(51) Int. Cl.

| A01H 1/00 | (2006.01) |
| C12N 15/00 | (2006.01) |
| C12N 15/63 | (2006.01) |
| C12N 15/82 | (2006.01) |
| A01H 5/00 | (2006.01) |

(52) U.S. Cl.
CPC ........ *C12N 15/8271* (2013.01); *C12N 15/8216* (2013.01); *C12N 15/8261* (2013.01)

(58) Field of Classification Search
None
See application file for complete search history.

(56) References Cited

U.S. PATENT DOCUMENTS

| 7,569,389 B2 | 8/2009 | Feldmann et al. |
| 2004/0034888 A1 | 2/2004 | Liu et al. |
| 2004/0172684 A1 | 9/2004 | Kovalic et al. |
| 2004/0214272 A1 | 10/2004 | La Rosa et al. |
| 2005/0044585 A1 | 2/2005 | Good et al. |
| 2006/0150283 A1 | 7/2006 | Alexandrov et al. |
| 2010/0162433 A1 | 6/2010 | McLaren et al. |
| 2011/0179519 A1 | 7/2011 | Coruzzi et al. |

FOREIGN PATENT DOCUMENTS

WO    2006030445    3/2006

OTHER PUBLICATIONS

Martin et al., "Two Cytosolic Glutamine Synthetase Isoforms of Maize Are Specifically Involved in the Control of Grain Production", "The Plant Cell", Nov. 2006, pp. 3252 vol. 18, Publisher: American Society of Plant Biologists.
Hsieh et al., "A PII-like protein in Arabidopsis: Putative role in nitrogen sensing", "Plant Biology", Nov. 1998, pp. 13965-13970, vol. 95, Publisher: The National Academy of Sciences.
Osanai et al., "Keeping in Touch with PII: PII-Interacting Proteins in Unicellular Cyanobacteria", "Plant Cell Physiol", 2007, pp. 908-914, vol. 48, No. 7, Publisher: Oxford University Press on behalf of Japanese Society of Plant Physiologists, Published in: Japan.
Verdoy et al, "Transgenic Medicago truncatula plants that accumulate proline display nitrogen-fixing activity with enhanced tolerance to osmotic stress", "Plant Cell Environ.", Oct. 2006, pp. 1913-1923, vol. 29, No. 10.
Yanagisawa, Shuichi, "Improved Nitrogen Assimilation Using Transcription Factors", Sep. 2004.
Yanagisawa et al., "Metabolic Engineering with Dof1 transcription factor in plants: Improved nitrogen assimilation and growth under low-nitrogen conditions", "The National Academy of Sciences of the USA", May 18, 2004, pp. 7833-7838, vol. 101, No. 20, Published in: Japan.

*Primary Examiner* — Phuong Bui
(74) *Attorney, Agent, or Firm* — Davis, Brown, Koehn, Shors & Roberts, P.C.; Kent A. Herink

(57) ABSTRACT

The present invention relates to transgenic plants that have increased nitrogen use efficiency, stress tolerance, or both and that have been transformed using a novel vector construct including nucleic acid sequences that modulate nitrogen use in plants. In various embodiments, the vector construct includes one or more nucleic acid sequences selected from the group consisting of SEQ ID NO: 2, 4, 7, 9, 11, 13, 15, 17, 22, 24, 26, 28, 30, 32, 34, 36, or 38. The invention also relates to isolated vectors for transforming plants and to antibodies used for detecting transformed plants. The invention also relates to methods of expressing in plants the nucleic acid molecules corresponding to the nucleic acid sequences that modulate nitrogen use in plants or are modulated by nitrogen conditions.

16 Claims, No Drawings

US 9,416,367 B2

PLANTS WITH IMPROVED NITROGEN UTILIZATION AND STRESS TOLERANCE

CROSS REFERENCE TO RELATED APPLICATION

This application is a divisional application of U.S. application Ser. No. 13/309,308, filed Dec. 1, 2011, which was a divisional application of U.S. application Ser. No. 11/977,768, filed, Oct. 26, 2007, which claims priority to U.S. Application Ser. No. 60/854,927, filed Oct. 27, 2006, which is incorporated herein in its entirety by this reference.

FIELD OF THE INVENTION

The invention relates generally to plants with improved nitrogen utilization and stress tolerance, more specifically, to corn plants transformed with a gene that improves stress tolerance and nitrogen uptake, metabolism or both.

BACKGROUND OF THE INVENTION

Plants require nitrogen during their vegetative and reproductive growth phases. Nitrogen is made available to the plant through soil mineralization, the application of nitrogen fertilizer, or both. It has been estimated, however, that between 50 and 70 percent of nitrogen applied to crops is lost from the plant-soil system [Peoples, M. B. et al., "Minimizing Gaseous Losses of Nitrogen," *In Nitrogen Fertilizer in the Environment* (Bacon, P. E., ed.) Marcel Dekker, pp. 565-606 (1995)]. Nitrogen is one of the most expensive plant nutrients to supply, nitrogen fertilizer is not always available at a reasonable cost, and excessive application of nitrogen fertilizer can result in pollution problems in runoff. Corn is an example of an agronomically important plant that often requires nitrogen fertilizers to perform at its genetic potential.

SUMMARY OF THE INVENTION

The present invention relates to transgenic plants that have increased nitrogen use efficiency, stress tolerance, or both, that have been transformed using a novel vector construct including nucleic acid sequences that modulate nitrogen use in plants. The invention also relates to isolated vectors for transforming plants and to antibodies for detecting expression of the nucleotide sequence of interest in the transformed plants. The invention also relates to methods of expressing in plants the nucleic acid molecules corresponding to the nucleic acid sequences that modulate nitrogen use in plants.

Specifically, vectors for transforming plants have been constructed using nucleotide sequences selected from the list consisting of SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38, as well as variants, fragments, and complements thereof. These vectors include a 5' DNA promoter sequence and a 3' terminator sequence, wherein the nucleic acid sequence, the DNA promoter sequence, and the terminator sequence are operatively coupled to permit transcription of the nucleotide sequence. In some embodiments, the promoter sequence may be a constitutive plant promoter or a tissue specific promoter.

The invention also includes polyclonal antibodies, comprising polyclonal antibodies to a polypeptide encoded by a nucleotide sequence selected from the list consisting of SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36; and SEQ ID NO: 38.

The invention also includes plants transformed with one or more nucleotide sequences selected from the list consisting of SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38, as well as variants and fragments thereof. The plant is selected from the group consisting of rice, corn, soybean, canola, wheat, alfalfa, barley, rye, cotton, sunflower, peanut, sweet potato, bean, pea, potato, oilseed rape, sorghum, forage grass, pasture grass, turf grass, and sugarcane. The invention also includes a component part of such plants, plant seed produced from such plants, and a plant seed transformed with a vector construct of the present invention.

The invention also includes a host cell transformed with one or more nucleotide sequences selected from the list consisting of SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36; and SEQ ID NO: 38. The host cell may be a bacterial cell or a plant cell.

The invention also includes a method of expressing a nucleic acid molecule modulated by nitrogen in a plant, said method comprising the steps of providing a transgenic plant or plant seed transformed with a vector construct according to the present invention, and growing the transgenic plant or a plant grown from the transgenic plant seed under conditions effective to express the nucleic acid molecule in said transgenic plant or said plant grown from the transgenic plant seed. Growing of the transgenic plant is effective in increasing nitrogen uptake of said transgenic plant or said plant grown from the transgenic plant seed, and/or in increasing efficiency of nitrogen utilization of said transgenic plant or said plant grown from the transgenic plant seed. The invention also includes the foregoing methods wherein a transgenic plant is provided or a transgenic seed is provided. The invention also includes the foregoing method wherein the plant is selected from the group consisting of rice, corn, soybean, canola, wheat, alfalfa, barley, rye, cotton, sunflower, peanut, sweet potato, bean, pea, potato, oilseed rape, sorghum, forage grass, pasture grass, turf grass, sugarcane.

The invention also includes a method of improving the stress tolerance of a plant by expressing a nucleic acid molecule modulated by nitrogen in a plant, said method comprising the steps of providing a transgenic plant or plant seed transformed with a vector construct according to the present invention and growing the transgenic plant or a plant grown from the transgenic plant seed under conditions effective to express the nucleic acid molecule in said transgenic plant or said plant grown from the transgenic plant seed.

The invention also includes a method of altering the morphology of a plant by expressing a nucleic acid molecule modulated by nitrogen in a plant, said method comprising the steps of providing a transgenic plant or plant seed transformed with a vector construct according to the present invention and growing the transgenic plant or a plant grown from the transgenic plant seed under conditions effective to express the nucleic acid molecule in said transgenic plant or said plant grown from the transgenic plant seed.

The invention also includes a vector construct, comprising a nucleotide sequence encoding an amino acid sequence selected from the list consisting of SEQ ID NO: 3, SEQ ID NO: 5, SEQ ID NO: 8, SEQ ID NO: 10, SEQ ID NO: 12, SEQ ID NO: 14, SEQ ID NO: 16, SEQ ID NO: 18, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37 and SEQ ID NO: 39, a 5' DNA promoter sequence, and a 3' terminator sequence, wherein the nucleotide sequence, the DNA promoter sequence, and the terminator sequence are operatively coupled to permit transcription of the nucleotide sequence.

The invention also includes a vector construct comprising a nucleotide sequence that is modulated by nitrogen in a plant, wherein said nucleotide sequence is selected from the group consisting of a nucleotide sequence selected from the list consisting of SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38; a nucleotide sequence having at least 95% sequence identity to the nucleotide sequence of SEQ ID NO: 2, SEQ ID NO: 4, SEQ ID NO: 7, SEQ ID NO: 9, SEQ ID NO: 11, SEQ ID NO: 13, SEQ ID NO: 15, SEQ ID NO: 17, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, or SEQ ID NO: 38, wherein said nucleotide sequence is modulated by nitrogen in a plant; a nucleotide sequence encoding an amino acid sequence selected from the list consisting of SEQ ID NO: 3, SEQ ID NO: 5, SEQ ID NO: 8, SEQ ID NO: 10, SEQ ID NO: 12, SEQ ID NO: 14, SEQ ID NO: 16, SEQ ID NO: 18, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, and SEQ ID NO: 39; and, a nucleotide sequence encoding an amino acid sequence having at least 95% sequence identity to the amino acid sequence of SEQ ID NO: 3, SEQ ID NO: 5, SEQ ID NO: 8, SEQ ID NO: 10, SEQ ID NO: 12, SEQ ID NO: 14, SEQ ID NO: 16, SEQ ID NO: 18, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, or SEQ ID NO: 39, wherein said nucleotide sequence is modulated by nitrogen in a plant, wherein said construct further comprises a 5' DNA promoter sequence and a 3' terminator sequence, wherein the nucleotide sequence, the DNA promoter sequence, and the terminator sequence are operatively coupled to permit transcription of the nucleotide sequence.

DETAILED DESCRIPTION OF PREFERRED EMBODIMENTS

The development of plant varieties that use nitrogen more efficiently will reduce the need for excessive inputs of nitrogen, save production costs for farmers, benefit farmers in developing countries who do not have access to fertilizer inputs, and reduce pollution associated with the application of excessive nitrogen fertilizers. One approach that has been used in the development of plant varieties with improved nitrogen utilization relies on conventional plant breeding techniques.

There is a need to develop plant cultivars that absorb and use nitrogen more efficiently. Plant scientists have adopted the shorthand term nitrogen use efficiency (NUE), and a variety of methods of measuring and evaluating NUE have been developed [Craswell, E. T. and Godwin, D. C. (1984) The efficiency of nitrogen fertilizers applied to cereals grown in different climates. In *Advances in Plant Nutrition* (Vol. 1) (Tinker, P. B. and Lauchli, A., eds), pp. 1-55, Praeger Publishers; Steenbjerg, F. and Jakobsen, S. T. (1963) Plant nutrition and yield curves. *Soil Sci*. 95, 69-90; Siddiqi, M. Y. and Glass, D. M. (1981) Utilization index: a modified approach to the estimation and comparison of nutrient utilization efficiency in plants. *J. Plant Nutr*. 4, 289-302; Moll, R. H. et al. (1982) Analysis and interpretation of factors which contribute to efficiency of nitrogen utilization. *Agron. J*. 74, 562-564]. There are differences in the definitions. Some definitions are based on total biomass while others are based on the weight of grain yielded. Another set of definitions uses the efficiency of extracting nitrogen from the soil. The efficiency with which applied nitrogen is used to improve grain yield may be measured by agronomic efficiency (AE), the product of physiological efficiency and utilization efficiency, or NUEg which is the product of uptake efficiency and utilization efficiency. Other definitions take physiological factors into account.

As used in this specification, the term nitrogen use efficiency, or NUE, is defined to include a measurable change in any of the main nitrogen metabolic pool sizes in the assimilation pathways (for example, may include a measurable change in one or more of the following: nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content), or where the plant is shown to provide the same or elevated yield at lower nitrogen fertilization levels, or where the plant is shown to provide elevated yields at the same nitrogen fertilization levels when compared to a plant that has not been transformed with a nitrogen-modulated nucleic acid construct of the invention. A "measurable change" can include an increase or a decrease in the amount of any component ("metabolic pool") of the nitrogen assimilation pathway. A change can include either a decrease or an increase in one or more metabolic pools in the pathway, or a decrease in one or more pools with a concomitant increase in one or more other pool(s), such as when one intermediate in the nitrogen assimilation pathway is being utilized for the purpose of generating another intermediate or product of the pathway. For example, in the conversion of glutamate to glutamine, the level of glutamate may decrease while the level of glutamine may increase. Thus, while not being bound by any particular theory or mechanism, any change in one or more of these pools indicates that nitrogen is being utilized more efficiently by the plant.

An increase in nitrogen utilization efficiency can be associated with about a 5%, about a 10%, 15%, 20%, 30%, 40%, 50%, 60%, 70%, 80%, 90%, 100%, 125%, 150%, about a 200% or greater measurable change in any of the main nitrogen metabolic pool sizes in the assimilation pathway. In one embodiment, the transgenic plants of the invention have an increased nitrogen uptake from the environment when compared to a plant that does not contain a nitrogen-modulated sequence of the invention. By "nitrogen modulated sequence" it is intended to mean a nucleotide or amino acid sequence that is modulated (e.g., increased or decreased, or upregulated or downregulated) in response to exposure to nitrogen, and by "nucleotide sequence that modulates nitrogen use", it is intended to mean a nucleotide sequence that codes for a protein that interacts with nitrogen metabolism.

The present invention further provides a method of improving stress tolerance in a plant by expressing one or more nitrogen-modulated nucleotide sequences within the plant. In one embodiment, the nitrogen-modulated nucleotide sequence is SEQ ID NO: 2, 4, 7, 9, 11, 13, 15, 17, 22, 24, 26, 28, 30, 32, 34, 36, or 38, or variants and fragments thereof. In another embodiment, the nitrogen-modulated nucleotide sequence is a nucleotide sequence that encodes SEQ ID NO: 3, 5, 8, 10, 12, 14, 16, 18, 23, 25, 27, 29, 31, 33, 35, 37, or 39, or variants and fragments thereof.

As used herein, the term "stress" or "stress condition" refers to the exposure of a plant, plant cell, or the like, to a physical or chemical agent or condition that has an adverse effect on metabolism, growth, development, propagation and/or survival of the plant (collectively "growth"). A stress can be imposed on a plant due, for example, to an environmental factor such as water (e.g., flooding, drought, dehydration), anaerobic conditions (e.g., a low level of oxygen), abnormal osmotic conditions, salinity or temperature (e.g., hot/heat, cold, freezing, frost), a deficiency of nutrients such as nitrogen or exposure to pollutants, or by a hormone, second messenger or other molecule. Anaerobic stress, for example, is due to a reduction in oxygen levels (hypoxia or anoxia) sufficient to produce a stress response. A flooding stress can be due to prolonged or transient immersion of a plant, plant part, tissue or isolated cell in a liquid medium such as occurs during monsoon, wet season, flash flooding or excessive irrigation of plants, or the like. A cold stress or heat stress can occur due to a decrease or increase, respectively, in the temperature from the optimum range of growth temperatures for a particular plant species. Such optimum growth temperature ranges are readily determined or known to those skilled in the art. Dehydration stress can be induced by the loss of water, reduced turgor, or reduced water content of a cell, tissue, organ or whole plant. Drought stress can be induced by or associated with the deprivation of water or reduced supply of water to a cell, tissue, organ or organism. Saline stress (salt stress) can be associated with or induced by a perturbation in the osmotic potential of the intracellular or extracellular environment of a cell. Osmotic stress also can be associated with or induced by a change, for example, in the concentration of molecules in the intracellular or extracellular environment of a plant cell, particularly where the molecules cannot be partitioned across the plant cell membrane.

An improvement in stress tolerance can be assessed by any quantitative or qualitative measure of plant performance under a given stress condition and is relative to the performance of a plant grown under the same stress conditions that has not been transformed with a nitrogen-modulated sequence of the invention. Thus, the plants may exhibit improved nitrogen contents, altered amino acid or protein compositions, vigorous growth characteristics, increased vegetative yields or better seed yields and qualities. These plants may be identified by examining any of following parameters: 1) the rate of growth, measured in terms of rate of increase in fresh or dry weight; 2) vegetative yield of the mature plant, in terms of fresh or dry weight; 3) the seed or fruit yield; 4) the seed or fruit weight; 5) the total nitrogen content of the plant; 6) the total nitrogen content of the fruit or seed; 7) the free amino acid content of the plant; 8) the free amino acid content of the fruit or seed; 9) the total protein content of the plant; and 10) the total protein content of the fruit or seed. The procedures and methods for examining these parameters are well known to those skilled in the art. These methods may involve enzymatic assays and immunoassays to measure enzyme/protein levels; assays to measure the amino acid composition, free amino acid pool or total nitrogen content of various plant tissues; measurement of growth rates in terms of fresh weight gains over time; or measurement of plant yield in terms of total dry weight and/or total seed weight.

Transformation of Bacterial or Plant Cells

Provided herein are novel nucleotide sequences that modulate nitrogen utilization efficiency in plants. Also provided are amino acid sequences of the nitrogen-modulated proteins of the invention.

The nitrogen-modulated nucleotide sequences of the invention may be modified to obtain or enhance expression in plant cells. The nitrogen-modulated sequences of the invention may be provided in expression cassettes for expression in the plant of interest. "Plant expression cassette" includes DNA constructs that are capable of resulting in the expression of a protein from an open reading frame in a plant cell. The cassette will include in the 5'-3' direction of transcription, a transcriptional initiation region (i.e., promoter) operably-linked to a DNA sequence of the invention, and a transcriptional and translational termination region (i.e., termination region) functional in plants. The cassette may additionally contain at least one additional gene to be cotransformed into the organism, such as a selectable marker gene. Alternatively, the additional gene(s) can be provided on multiple expression cassettes. Such an expression cassette is provided with a plurality of restriction sites for insertion of the nitrogen-modulated sequence to be under the transcriptional regulation of the regulatory regions.

By "promoter" is intended a nucleic acid sequence that functions to direct transcription of a downstream coding sequence. The promoter, together with other transcriptional and translational regulatory nucleic acid sequences (also termed as "control sequences"), are necessary for the expression of a DNA sequence of interest. Preferably, the promoter is one that is known to stimulate transcription in the organism into which the nucleotide sequence of the invention is being introduced.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the nucleic acid sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, "operably linked" means that the nucleic acid sequences being linked are contiguous and, where necessary to join two protein coding regions, contiguous and in the same reading frame.

In one embodiment, the promoter is a constitutive promoter. Suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); promoters of Chlorella virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171); ubiquitin (Christensen et al.

(1989) *Plant Mol. Biol.* 12:619-632 and Christensen et al. (1992) *Plant Mol. Biol.* 18:675-689), including the TrpPro5 promoter (U.S. patent application Ser. No. 10/377,318; filed Mar. 16, 2005); pEMU (Last et al. (1991) *Theor. Appl. Genet.* 81:581-588); MAS (Velten et al. (1984) *EMBO J.* 3:2723-2730); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO 97/41228); and promoters of various *Agrobacterium* genes (see U.S. Pat. Nos. 4,771,002; 5,102,796; 5,182,200; and 5,428,147).

In another embodiment, the promoter is a tissue-specific promoter. A list of commonly-used tissue-specific promoters can be found in Reviewed in Moore et al. (2006) *Plant J.* 45(4):651-683, which is herein incorporated by reference in its entirety.

Often, such constructs will also contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence.

Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the nitrogen-modulated sequence of the present invention, or may be derived from another source. Convenient termination regions are available from the Ti-plasmid of *A. tumefaciens*, such as the octopine synthase and nopaline synthase termination regions, or the potato proteinase inhibitor II sequence (PinII) as described in Liu et al. (2004) *Acta Biochim Biophys Sin* 36(8):553-558. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "nucleotide sequence of interest" (a nucleotide sequence engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science*, 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Altered or Improved Variants Useful in the Constructs of the Invention

It is recognized that nucleotide and amino acid sequences useful in the present invention may be altered by various methods, and that these alterations may result in sequences encoding proteins with amino acid sequences different than that encoded by the nitrogen-modulated sequences disclosed herein.

Nucleotide sequences useful in the present invention include the sequences set forth in SEQ ID NO: 2, 4, 7, 9, 11, 13, 15, 17, 22, 24, 26, 28, 30, 32, 34, 36, and 38, and variants, fragments, and complements thereof. As used herein, the term "nucleotide sequence" or "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecules can be single-stranded or double-stranded, but preferably are double-stranded DNA. By "complement" is intended a nucleotide sequence that is sufficiently complementary to a given nucleotide sequence such that it can hybridize to the given nucleotide sequence to thereby form a stable duplex. The corresponding amino acid sequences for the nitrogen-modulated proteins encoded by these nucleotide sequences are set forth in SEQ ID NO: 3, 5, 8, 10, 12, 14, 16, 18, 23, 25, 27, 29, 31, 33, 35, 37, and 39, as well as variants and fragments thereof. The invention also encompasses the use of nucleic acid molecules comprising nucleotide sequences encoding partial-length nitrogen-modulated proteins, and complements thereof.

Nucleic acid molecules that are fragments of these nitrogen-modulated nucleotide sequences are also useful in the present invention. By "fragment" is intended a portion of a nucleotide sequence encoding a nitrogen-modulated protein. A fragment of a nucleotide sequence may encode a biologically active portion of a nitrogen-modulated protein, or it may be a fragment that can be used as a hybridization probe or PCR primer using methods disclosed below. Nucleic acid molecules that are fragments of a nitrogen-modulated nucleotide sequence comprise at least about 15, 20, 50, 75, 100, 200, 300, 350, or at least about 400 contiguous nucleotides, or up to the number of nucleotides present in a full-length nitrogen-modulated nucleotide sequence disclosed herein depending upon the intended use. By "contiguous" nucleotides is intended nucleotide residues that are immediately adjacent to one another.

Polypeptides that are fragments of these nitrogen-modulated polypeptides are also useful in the present invention. By "fragment" is intended a portion of an amino acid sequence encoding a nitrogen-modulated protein as set forth SEQ ID NO: 3, 5, 8, 10, 12, 14, 16, 18, 23, 25, 27, 29, 31, 33, 35, 37, or 39, and that retains nitrogen utilization efficiency. A biologically active portion of a nitrogen-modulated protein can be a polypeptide that is, for example, 10, 25, 50, 100, 125, 150, 175, 200, 250, 300, 350, 400 or more amino acids in length. Such biologically active portions can be prepared by recombinant techniques and evaluated for nitrogen utilization efficiency. As used here, a fragment comprises at least 8 contiguous amino acids of SEQ ID NO: 3, 5, 8, 10, 12, 14, 16, 18, 23, 25, 27, 29, 31, 33, 35, 37, or 39. The invention encompasses other fragments, however, such as any fragment in the protein greater than about 10, 20, 30, 50, 100, 150, 200, 250, 300, 350, or 400 amino acids.

The invention also encompasses the use of variant nucleic acid molecules, or variant amino acid sequences, in the methods and compositions of the inventions. "Variants" of the nitrogen-modulated nucleotide sequences include those sequences that encode a nitrogen-modulated protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the nitrogen-modulated proteins disclosed in the present invention as discussed below. Variant proteins useful in the present invention are biologically active, that is they retain the desired biological activity of the native protein, that is, nitrogen utilization efficiency and/or improved stress tolerance.

By "variants" is intended proteins or polypeptides having an amino acid sequence that is at least about 60%, 65%, about 70%, 75%, 80%, 85%, or 90%, 91%, 92%, 93%, 94%, 95%, 96%, 97%, 98% or 99% identical to the amino acid sequence of SEQ ID NO: 3, 5, 8, 10, 12, 14, 16, 18, 23, 25, 27, 29, 31, 33, 35, 37, or 39. Variants also include polypeptides encoded by a nucleic acid molecule that hybridizes to the nucleic acid molecule of SEQ ID NO: 2, 4, 7, 9, 11, 13, 15, 17, 22, 24, 26, 28, 30, 32, 34, 36, or 38, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retain nitrogen utilization efficiency and/or improved stress tolerance.

Preferred nitrogen-modulated proteins useful in the present invention are encoded by a nucleotide sequence sufficiently identical to the nucleotide sequence of SEQ ID NO: 2, 4, 7, 9, 11, 13, 15, 17, 22, 24, 26, 28, 30, 32, 34, 36, or 38. The term "sufficiently identical" is intended an amino acid or nucleotide sequence that has at least about 60% or 65% sequence identity, about 70% or 75% sequence identity, about 80% or 85% sequence identity, or about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to nitrogen-modulated nucleic acid molecules of the invention. BLAST protein searches can be performed with the BLASTX program, score=50, wordlength=3, to obtain amino acid sequences homologous to nitrogen-modulated protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

A preferred program is GAP version 10, which used the algorithm of Needleman and Wunsch (1970) *J. Mol. Biol.* 48:443-453. GAP Version 10 may be used with the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 Scoring Matrix. Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The skilled artisan will further appreciate that changes can be introduced by mutation into the nucleotide sequences of the invention thereby leading to changes in the amino acid sequence of the encoded nitrogen-modulated protein, without altering the biological activity of the protein. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, preferably nonessential amino acid residues. A "nonessential" amino acid residue is a residue that can be altered from the wild-type sequence of a nitrogen-modulated protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues. Examples of residues that are conserved and that may be essential for protein activity include, for example, residues that are identical between all proteins contained in an alignment of similar or related sequences known to be involved in nitrogen assimilation. Examples of residues that are conserved but that may allow conservative amino acid substitutions and still retain activity include, for example, residues that have only conservative substitutions between all proteins contained in an alignment of similar or related sequences known to be involved in nitrogen assimilation.

Alternatively, variant nucleotide sequences can be made by introducing mutations randomly along all or part of the coding sequence, such as by saturation mutagenesis, and the resultant mutants can be screened for ability to confer nitrogen utilization efficiency to identify mutants that retain activity. Following mutagenesis, the encoded protein can be expressed recombinantly, and the activity of the protein can be determined using standard assay techniques.

Using methods such as PCR, hybridization, and the like, corresponding nitrogen-modulated sequences can be identified, such sequences having substantial identity to the sequences of the invention. See, for example, Sambrook J., and Russell, D. W. (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY). In a hybridization method, all or part of the nitrogen-modulated nucleotide sequence can be used to screen cDNA or genomic libraries. Methods for construction of such cDNA and genomic libraries are generally known in the art and are disclosed in Sambrook and Russell, 2001, supra.

Variants and fragments of the nucleotide or amino acid sequences of the present invention generally will encode protein fragments that retain the biological activity of the full-length nitrogen-modulated protein; i.e., retain nitrogen utilization efficiency. By "retains nitrogen utilization efficiency" is intended that the variant or fragment will have at least about 30%, at least about 50%, at least about 70%, or at least about 80% of the nitrogen utilization efficiency and/or stress tolerance of the full-length nitrogen-modulated protein disclosed herein as SEQ ID NO: 3, 5, 8, 10, 12, 14, 16, 18, 23, 25, 27, 29, 31, 33, 35, 37, or 39, or the full-length nitrogen-modulated nucleotide sequence disclosed herein as SEQ ID NO: 2, 4, 7, 9, 11, 13, 15, 17, 22, 24, 26, 28, 30, 32, 34, 36, or 38. Methods for monitoring nitrogen utilization efficiency include detecting a change in any of the main nitrogen metabolic pool sizes in the assimilation pathways (for example, a measurable change in nitrate, nitrite, ammonia, glutamic acid, aspartic acid, glutamine, asparagine, lysine, leucine, threonine, methionine, glycine, tryptophan, tyrosine, total protein content of a plant part, total nitrogen content of a plant part, and/or chlorophyll content) or detecting the ability of a plant to provide the same or elevated yield at lower nitrogen fertilization levels, or the ability of a plant to provide elevated yields at the same nitrogen fertilization levels when compared to a plant that does not contain or express a nitrogen-modulated sequence of the invention. The designation of "same" or "lower" nitrogen fertilization levels refers to the level of nitrogen generally applied to a plant not expressing a nitrogen-modulated sequence of the invention. Sufficient nitrogen levels are known in the art for the majority, if not all, plant varieties of interest. Additional guidance may be found in, for example, Hewitt (1966) *Sand and Water Culture Methods Used in the Study of Plant Nutrition,* 2nd ed., Farnham Royal (Bucks), Commonwealth Agricultural Bureaux; and, Hewitt (1975) *Plant Mineral Nutrition,* London, English University Press.

The polypeptide sequences useful in the present invention may be altered in various ways including amino acid substitutions, deletions, truncations, and insertions. Methods for such manipulations are generally known in the art. For example, amino acid sequence variants of the nitrogen-modulated proteins disclosed herein can be prepared by mutations in the nucleotide sequences. This may also be accomplished by one of several forms of mutagenesis and/or in directed evolution. In some aspects, the changes encoded in the amino acid sequence will not substantially affect function of the protein. Such variants will possess the desired nitrogen utilization efficiency. However, it is understood that the ability of the nitrogen-modulated sequences of the invention to alter or improve nitrogen utilization may be further improved by one use of such techniques upon the compositions of this invention. For example, one may express the nucleotide sequences disclosed herein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), transform it into plants as described elsewhere herein, and measure nitrogen utilization efficiency.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest, (2) introduce a binding domain, enzymatic activity, or epitope to facilitate either protein purification, protein detection, or other experimental uses known in the art, or, (3) target secretion or translation of a protein to a subcellular organelle, such as the periplasmic space of gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different nitrogen-modulated protein coding regions can be used to create a new nitrogen-modulated protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the nitrogen-modulated sequence useful in the present invention and other known nitrogen-modulated sequences to obtain a new sequence coding for a protein with an improved property of interest, such as improved nitrogen utilization. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Plant Transformation

Methods of the invention involve introducing one or more nitrogen-modulated nucleotide sequences into a plant. In some embodiments, only one of the nitrogen-modulated sequences disclosed herein is introduced into the plant. In other embodiments, at least 2, at least 3, at least 4, or more of the sequences are introduced. Where multiple sequences are introduced, each of the nucleotide sequences is non-identical. Two nucleotide sequences are considered non-identical if they differ in at least one nucleotide position. Thus, non-identical nucleotide sequences include two or more different nucleotide sequences that each encodes the same amino acid sequence (e.g., one or more has been optimized for expression in the plant), as well as two or more different nucleotide sequences that encode at least two different amino acid sequences.

By "introducing" is intended to present to the plant one or more constructs comprising the one or more nitrogen-modulated sequences in such a manner that the construct(s) gain(s) access to the interior of a cell of the plant. The methods of the invention do not require that a particular method for introducing a nucleotide construct to a plant is used, only that the nucleotide construct(s) gain(s) access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (i.e., antibiotics, such as spectinomycin and kanamycin). The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can then be used to confirm the presence of the integrated heterologous gene of interest in the genome of transgenic plant.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Transformation of bacterial cells is accomplished by one of several techniques known in the art, including but not limited to electroporation or chemical transformation (see, for example, Ausubel, ed. (1994) *Current Protocols in Molecular Biology*, John Wiley and Sons, Inc., Indianapolis, Ind.). Markers conferring resistance to toxic substances are useful in identifying transformed cells (having taken up and expressed the test DNA) from non-transformed cells (those not containing or not expressing the test DNA).

In one aspect of the invention, the nucleotide sequences of the invention are useful as markers to assess transformation of bacterial or plant cells. In this manner, transformation is assessed by monitoring nitrogen utilization efficiency as described above.

Transformation of plant cells can be accomplished in similar fashion. By "plant" is intended whole plants, or component parts including plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Methods to Increase Plant Yield by Modulating Nitrogen Utilization

Methods for increasing plant yield are provided. The methods comprise introducing into a plant or plant cell a nitrogen-modulated nucleotide sequence disclosed herein such that an increase in nitrogen utilization efficiency corresponds to an increase in plant yield. As defined herein, the "yield" of the plant refers to the quality and/or quantity of biomass produced by the plant. By "biomass" is intended any measured plant product (e.g., any component part of a plant, such as seed, stalk, root, grain, leaf, etc.). An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in plant yield compared to the yield of a plant into which a nucleotide sequence that modulates use of nitrogen of the invention has not been introduced.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, grasses (such as turf grasses, forage grasses, or pasture grasses), ornamentals, fruit trees, and conifers.

Vegetables include, but are not limited to, onions, tomatoes, lettuce, green beans, lima beans, peas, and members of the genus *Curcumis* such as cucumber, cantaloupe, and muskmelon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated nucleotide sequences at the earlier stage before transplanting into the soil (Sambrook and Russell (2001) *Molecular Cloning: A Laboratory Manual*, Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragments to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by the nucleotide sequence of the invention is then tested by hybridizing the filter to a radioactive probe derived from a polynucleotide of the invention, by methods known in the art (Sambrook and Russell, 2001, supra)

Western blot and biochemical assays and the like may be carried out on the transgenic plants to determine the presence of protein encoded by the nitrogen-modulated gene by standard procedures (Sambrook and Russell, 2001, supra) using antibodies that bind to one or more epitopes present on the nitrogen-modulated protein. For example, the polyclonal antibodies generated by the methods of the present invention can be used to detect the presence of a nitrogen-modulated protein.

Antibodies

Antibodies to the polypeptides useful in the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Experimental

Materials and Methods

The majority of the starting genetic material for this project was provided in the form of maize expressed sequence tags, or "ESTs", derived from a microarray experiment to identify potential genes up- or down-regulated in response to nitrogen. The microarray experiment identified several hundred possible candidates for possible use in transformations. While these sequences were predictive of gene transcription as a response to nitrogen fluctuations, they did not provide a firm identification of genes that were regulated in response to nitrogen levels or genes that regulate nitrogen levels. The candidate ESTs from the microarray experiment were screened based on genomic selection criteria to analyze and determine a small number of priority candidates for subsequent use in transgenic expression as described in this specification. All EST sequences that were entered into the project (i.e., "project genes") were first examined to identify open reading frames that could encode a protein that was responsive to plant nitrogen levels. Multiple open reading frames were typically present within an EST. Ultimately, individual project genes were selected based on multiple criteria, including size of open reading frame wherein longer open reading frames were preferentially selected, and predicted function of translated genes, wherein individual open reading frames were translated and then subjected to a BLAST search to identify protein homologues. In cases where homologues were identified, we inferred that the gene was likely to encode a protein with a similar function. This information was used to assess if genes might encode protein functions with relevance to nitrogen assimilation in plants.

By this selection process, an individual gene target was selected from each EST. The complete gene sequence selected from each EST is disclosed in the following examples. One of the EST sequences (N-EST77-A01) was used as a source for two different genes that were entered into the project (N-EST77A and N-EST77B) and for one other EST (EST N-EST76-H12). We discovered that the EST could be modified to generate an open reading frame that is longer than the reading frames present in the unmodified EST. In summary, three open reading frames were combined to create one longer gene ("N-EST76A").

In some cases, a DNA sample provided from the microarray experiment was used as the source material for all subsequent DNA cloning steps. In cases where the EST sample was not suitable, synthetic sequences were generated. The N-EST76b gene was ordered as a synthetic gene from the vendor Blue Heron Biotechnology, Inc. (Bothell, Wash.). The gene sequence for each EST and each synthetic gene was confirmed by DNA sequencing prior to subcloning each gene for protein overexpression.

Protein Overexpression and Purification

Each of the genes selected for the project were subcloned into an expression vector that facilitates protein overexpression in *E. coli*. The protein overexpression was carried out to allow individual proteins to be purified. The purified proteins can be used to generate polyclonal antibodies against each protein in a pair of rabbits. Finally, the polyclonal antibodies can be used to detect the presence of target proteins in transgenic plants.

Using methods known in the art, each of the project genes was subcloned into the *E. coli* expression vector pRSF1b (Invitrogen Corporation, Carlsbad, Calif.). Resulting clones were confirmed by DNA sequencing, and used to induce expression of each protein in *E. coli*. The expressed His-tagged protein was then purified as known in the art using a cobalt affinity resin (Clontech Laboratories, Inc., Mountain View, Calif.).

Plant Transformation

Representative project genes were subcloned into vectors to carry out *Agrobacterium*-mediated transformation of maize. Following vector construction and transformation of *Agrobacterium*, the vectors were confirmed by Southern blot by methods known in the art. Positive *Agrobacterium* strains that passed these tests were then grown on a solid medium to produce cell counts for large-scale transformation experiments.

The following examples describe the methods for plant vector construction and plant transformation.

Vector Construction for Plant Transformation

The open reading frame (ORF) for each project gene is amplified by PCR from the maize EST sequence or synthetic gene. Restriction sites (BamH I and Asc I, for example) are added to each end of the ORF during PCR. Additionally, the nucleotide sequence ACC is added immediately 5' to the start codon of the gene to increase translational efficiency (Kozak (1987) *Nucleic Acids Research* 15:8125-8148; Joshi (1987) *Nucleic Acids Research* 15:6643-6653). The PCR product is subcloned into an intermediate vector (for example, pRSF-1b) and sequenced, using techniques well known in the art, to ensure that no mutations are introduced during PCR. The plasmid containing the project gene is digested with, for example, BamH I and Pst I and a fragment containing the intact ORF is isolated and purified.

The purified DNA fragment containing the project ORF is then subcloned into a plasmid such as pSB11 (Japan Tobacco, Inc.), for example at a BamH I and Pst I site, to complete the plant expression vector. The plant expression vector contains, for example, a *Tripsacum* ubiquitin promoter, TripPro5 promoter (U.S. patent application Ser. No. 11/377,318 filed Mar. 16, 2006, incorporated herein by this reference) and the PinII terminator (An et al. (1989) *The Plant Cell* 1:115-122) to form the final plasmid, referred to herein as pSB11-1A. pSB11-IA is organized such that the DNA fragment containing, for example, the promoter—NUE gene—terminator construct may be excised by appropriate restriction enzymes and also used for transformation into plants, for example, by aerosol beam injection. The structure of pSB11-1A is verified by restriction digest and gel electrophoresis, as well as by sequencing across the various cloning junctions.

The plasmid is mobilized into *Agrobacterium tumefaciens* strain LBA4404 which also harbors the plasmid pSB1 (Japan Tobacco, Inc.), using triparental mating procedures well known in the art, and plated on media containing antibiotic. Plasmid pSB11-1A carries spectinomycin resistance but is a narrow host range plasmid and cannot replicate in *Agrobacterium*. Antibiotic resistant colonies arise when pSB11-1A integrates into the broad host range plasmid pSB1 through homologous recombination. The resulting cointegrate product is verified by Southern hybridization. The *Agrobacterium* strain harboring the cointegrate can be used to transform plants, for example, by the PureIntro method (Japan Tobacco, Inc.).

Transformation of Plant Cells by *Agrobacterium*-Mediated Transformation

Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants. At this time, leaf samples are isolated and the presence of the gene of interest is confirmed by PCR.

All plants generated in this manner were grown to seed set and crossed with pollen isolated from with Hi-II plants (Iowa State University, Ames, Iowa). The fertilized plants were grown until maturity. Mature seeds were harvested from individual plants and saved for future testing in the T1 generation, if necessary.

Protein Expression in Transgenic Plants

Protein expression in representative transgenic maize events was estimated by Western blot. Briefly, leaf samples were taken after 4 weeks of growth in the greenhouse and immediately frozen on dry ice. Total protein was extracted (P-PER plant protein extraction kit, Pierce) and the protein concentration determined by Bradford assay. Individual plant protein samples were separated by electrophoresis, transferred to nitrocellulose, and the immobilized proteins were contacted with rabbit polyclonal antiserum using methods known in the art. Bound antibody complexes were visualized with the ECL Plus Western Blotting detection system (GE Healthcare Bio-Sciences Corp., Piscataway, N.J.).

Nitrogen Assay Methods

In preparation for nitrogen assays, leaves were sliced from plants two or four weeks after transfer from tissue culture to the greenhouse (or four weeks from germination for T1 plants). The material was snap frozen on dry ice and stored at −80° C. prior to processing.

Nitrate

Fifty milligrams of leaf material (fresh weight, no midrib) were freeze-dried for dry weight determination. The dehydrated leaf tissue was then ground in the presence of fresh Milli Q water using a MiniBeadbeater-96™ and 2.3 mm stainless-steel beads. The ground leaf tissue was filtered through a 0.45 µm Polyvinylidene Fluoride (PVDF) filter and injected into an Agilent 1100 HPLC running a mobile phase of a mixture of 1.8 mM sodium carbonate and 1.7 mM sodium bicarbonate at 1.5 ml/min. Ions were separated using an IonPac AS9-SC ion chromatography column equipped with a guard column. Analysis was performed using anion auto-suppressed conductivity with a self-regenerating suppressor operating in recycle mode. Samples were compared to internal standards included in each sample run.

Ammonium

Fifty milligrams of leaf material (fresh weight, no midrib) were ground in the presence of 60% methanol using a Mini-Beadbeater-96™ and 2.3 mm stainless-steel beads. The ground leaf tissue was filtered through a 0.45 µm Polyvinylidene Fluoride (PVDF) filter and injected into an Agilent 1100 HPLC equipped with a 3.3 m, 63° C. stainless steel coil and cooled autosampler. The mobile phase contained 3 mM o-phthalaldehyde (OPA), 10 mM β-mercaptoethanol, and 100 mM phosphate buffer (pH6.8) running at 0.4 ml/min. Fluorescence (excitation 410 nm and emission 470 nm) and diode array detection (410 nm) were used for the quantification of ammonium in the leaf extracts. Internal ammonium standards were included in each run for comparison.

Amino Acids by HPLC

Fifty milligrams of leaf material (fresh weight, no midrib) were freeze-dried for dry weight determination. The dehydrated leaf tissue was then ground in the presence of fresh Milli Q water using a MiniBeadbeater-96™ and 2.3 mm stainless-steel beads. The ground leaf tissue was filtered through a 0.45 µm Polyvinylidene Fluoride (PVDF) filter and injected into an Agilent 1100 HPLC using a Zorbax Eclipse AAA, 4.6×75 mm reverse phase column equipped with a guard column. A cooled autosampler was used to mix the leaf extract with 400 mM borate buffer (pH 10.2), 1% o-phthaladehyde/1% 3-mercaptopropionic acid in methanol, which was then diluted with water prior to injection. The details of the injector program are as follows: 0.5 µl sample are added to 2.5 µl borate buffer and mixed at maximum speed two times. After a 0.5 minute hold, the needle is placed in water to remove residue from the tip and then 0.5 µl OPA solution is added. The combined 3.5 µl is mixed at maximum speed six times. The needle is again placed in water to rinse the tip and then placed into a vial containing fresh water. Next, 32 µl Milli Q water are added to the sample mixture, and 18 µl are mixed at maximum speed two times. The sample solution is then injected into the HPLC with the pump running a 2 ml/min mobile phase of 40 mM Na2HPO4 (pH 7.8) (A) with a gradient from 0 to 26% acetonitrile/methanol/water (45:45:10) (B) in five minutes followed by a 100% hold B for two minutes then 100% A for two minutes. Quantification of asparagine, glutamine, glutamic acid, and aspartic acid was performed by diode array detection (328 to 348 nm) and fluorescence detection (excitation 340 nm, emission 450 nm). Samples were compared to asparagine, glutamine, glutamic acid, and aspartic acid internal standards included in each sample run.

Total Amino Acids

Fifty milligrams of leaf material (fresh weight, no midrib) were freeze-dried for dry weight determination. The dehydrated leaf tissue was then ground in the presence of fresh Milli Q water using a MiniBeadbeater-96™ and 2.3 mm stainless-steel beads. The ground leaf tissue was filtered through a 0.45 µm Polyvinylidene Fluoride (PVDF) filter. Dilutions of leaf extract were performed in water, and ninhydrin reagent solution (ninhydrin and hydrindantin in DMSO and lithium acetate buffer, pH 5.2) was added. The samples were then sealed with a thick foil tape, heated for ten minutes at 90° C., cooled for exactly two minutes, and read in a spectrophotometer at 590 nm. Values were compared with internal standards included during each sample analysis.

Total Protein

Fifty milligrams of leaf material (fresh weight, no midrib) were freeze-dried for dry weight determination. The dehydrated leaf tissue was then ground in the presence of fresh Milli Q water using a MiniBeadbeater-96™ and 2.3 mm stainless-steel beads. The ground leaf tissue was filtered through a 0.45 µm Polyvinylidene Fluoride (PVDF) filter. Bio-Rad Protein Dye was added to leaf samples diluted in water, and a Bradford protein assay was performed and read in the spectrophotometer at 595 nm vs. internal protein standards included in the assay.

Chlorophyll

Fifty milligrams of leaf material (fresh weight, no midrib) were ground in the presence of 60% methanol using a MiniBeadbeater-96™ and 2.3 mm stainless-steel beads. The ground leaf tissue was filtered through a 1.0 µm A/B glass fiber filter, and 100 µl extract was placed in a Corning 3370 flat bottom microplate and read in spectrophotometer with wells blanked with an equivalent volume of 60% methanol. SoftMax Pro software was used to convert the light pathlength to 1 cm. Calculations of chlorophyll content were performed using equations from Porra, R. J. *Photosynthesis Research,* 73: 149-156, 2002.

Example 1

Identification of Candidate ESTs

The nucleotide sequence information for each of the candidate nitrogen-modulated genes was generated in a differential nitrogen microarray experiment conducted at the direction of applicant by Dr. Pat Schnable at Iowa State University. This microarray experiment was used as an initial screen to select a sub-set of ESTs that may be related to nitrogen conditions.

From the large number of EST sequences showing some difference in the microarray (136 with both 3' and 5' data), further selections were made following a bioinformatics analysis. This analysis included checking for nucleotide sequence similarities in the International Nucleotide Sequence Database (housed at NCBI), checking for predicted protein similarities in the protein databases, such as NCBI and Swisspro, exploring information concerning known or predicted function, and checking the nucleotide and protein databases at the patent office. Using the results of these analyses, as well as supporting key information, a subset of ESTs was selected for transgenic overexpression in corn in relation to nitrogen use efficiency. For each of the EST sequences, an open reading frame was identified and translated into an amino acid sequence. A list of the candidate nitrogen-modulated sequences is provided in Table 1.

Vector Construction for Overexpression of Nitrogen-Modulated Sequences in Plants An open reading frame for each of the candidate nitrogen-modulated ESTs was subsequently introduced into vectors for plant expression. Using an approach well-known in the art, two different selectable marker systems which allow selection of transformed plants in the presence of a selection agent were employed.

Maize Transformation with Nitrogen-Modulated Genes

The plant vectors described are useful for plant transformation experiments to introduce the nitrogen-modulated genes into the maize genome using the methods described above.

TABLE 1

Nitrogen-modulated sequences

| EST Name | EST Sequence (SEQ ID NO:) | Open reading frame (SEQ ID NO:) | Protein sequence (SEQ ID NO:) | pAX number |
|---|---|---|---|---|
| N-EST213 | 1 | 2 | 3 | pAX2411 |
|  |  |  |  | pAX2410 |
| N-EST45-C08 |  | 4 | 5 | pAX3404 |
| N-EST77-A[1] | 6 | 7 | 8 | pAX3405 |
| N-EST77-B[1] | 6 | 9 | 10 | pAX3406 |
| N-EST61-A10 |  | 11 | 12 | pAX2422 |
| N-EST88-H03 |  | 13 | 14 | pAX2425 |
| N-EST15 |  | 15 | 16 | pAX2437 |
| N-EST42-B12 |  | 17 | 18 | pAX2435 |

TABLE 1-continued

Nitrogen-modulated sequences

| EST Name | EST Sequence (SEQ ID NO:) | Open reading frame (SEQ ID NO:) | Protein sequence (SEQ ID NO:) | pAX number |
|---|---|---|---|---|
| N-EST76a[2] | 19 | 22 | 23 | pAX2433 |
| N-EST76b[2] | 19 | 24 | 25 | pAX2431 |
| N-EST31-A10 |  | 26 | 27 | pAX2441 |
| N-EST43 |  | 28 | 29 | pAX2443 |
| N-EST264 |  | 30 | 31 | pAX2437 |
| N-EST28 |  | 32 | 33 | pAX2439 |
| N-EST13A-A08 |  | 34 | 35 | pAX2454 |
| N-EST13E-E07 |  | 36 | 37 | pAX2457 |
| N-EST55C-C10 |  | 38 | 39 | pAX2460 |

[1]See Example 2
[2]See Example 3

Example 2

Two Maize Proteins N-EST77A, N-EST77B

This invention describes the use of a maize gene sequence (from EST N-EST77-A01) to confer enhanced nitrogen utilization in transgenic maize (*Zea mays*). Two open reading frames are joined to a highly active plant promoter and a terminus to express each protein following integration into the maize genome. The ectopically expressed proteins will enhance the maize plant's ability to utilize available nitrogen.

Bioinformatics analysis revealed that there was no significant sequence homology with other sequences in the NCBI database. One portion showed some homology to a CCAAT-binding transcription factor in other species but not in maize. When the nucleotide sequence was received from the microarray experiment, there was also a predicted protein sequence. The predicted protein is referred to herein as N-EST77A. Examination of the nucleotide sequence indicated that the nucleotide could code for another protein (subsequently confirmed), and that protein sequence is referred to as N-EST77B. This second protein was not predicted in any information received from the microarray experiment.

For expression of N-EST77B, the first amino acid was changed from a leucine to a methionine to improve protein expression.

Example 3

Maize Protein N-EST76

This Example describes the use of a maize gene sequence (from EST N-EST76-H12) to confer enhanced nitrogen utilization in transgenic maize (*Zea mays*). This particular EST possesses part of the nucleotide sequence that is homologous to the so-called "bZIP" class of transcription factors. For this invention, two separate gene constructs are overexpressed in plants. One construct ("N-EST76a") contains the modified version of the N-EST76-H12 EST to allow a longer open reading frame to be expressed in maize. This modified gene contains 3 substitutions when compared to the gene sequence in the native EST. A second gene is also created which adds a basic region leucine zipper sequence to the 3' end of the gene. The resulting gene is referred to as "N-EST76b"

The full-length clone sequence appeared to contain two different regions that code for proteins, protein I of 108 amino acids and protein II of 122 amino acids. It was recognized, however, that if the full-length clone had not been sequenced accurately and a mistake had been made in the sequencing in the middle of the clone, a frameshift may have artificially generated a new start codon when it should not be there, thus suggesting two regions when there is only one longer region. To accommodate this possibility, the sequence analysis was done assuming that both the two shorter regions and the one longer region existed. Briefly, the nucleotide sequence searches returned results that indicated that the "I" sequence had some homology with a hypothetical protein from rice (genomic DNA from the rice genome program), and minor homology with some putative bZIP TFs. The nucleotide patent database search showed that sequence I had some homology (E=2e-06) with sequences that were noted to be transcription factors (e.g. WO03007699). A predicted amino acid sequence for I from the microarray assay was used to search against the databases and no significant hits were found. However, when the nucleotide sequence I was re-translated using GenBank tools, or the ExPasy tool, the predicted protein sequences were found to have: (1) Hits against the GenBank protein dbase (e.g. E=9e-09) with suggested function being a bZIP transcription factor; and (2) hits against the patent protein database (e.g. E=7e-05) with function being associated with a bZIP transcription factor (especially from rice), or an ABA-responsive element-binding protein (mostly from *Arabidopsis*, e.g. U.S. Pat. No. 6,245,905).

Confirmation of DNA Sequence

The DNA construct that contained N-EST76-H12 was sequenced to confirm the sequence provided from the microarray assay. This sequencing effort revealed a single nucleotide substitution at position 1121 of SEQ ID NO: 19, in which a "G" is present in place of a "C". This substitution is located in an open reading frame described for N-EST76, and leads to the substitution of a glutamine for a glutamic acid in the protein sequence. The correct DNA sequence for the full N-EST76-H12 EST is represented in SEQ ID NO: 19.

Cloning Strategy to Generate N-EST76a and N-EST76b

The DNA sequence in N-EST76-H12 contains 3 open reading frames that are separated by two stop codons and one frameshift. The cloning strategy employed was to eliminate both stop codons and the frameshift to produce a continuous open reading frame that is more similar to known bZIP proteins and is thus more likely to function properly when expressed. Additionally, bZIP proteins typically contain a basic region leucine zipper at the C-terminal end of the protein. N-EST76-H12 does not contain such a domain. Thus, a second protein was created which adds a basic region leucine zipper domain to the end of the N-EST76 protein.

Elimination of Stop Codons and Frameshift in N-EST76-H12

For this Example, the maize sequence described in the EST N-EST76-H12 (SEQ ID NO:19) was modified to produce a longer open reading frame that is more homologous to full-length bZIP proteins. This required 3 modifications to the N-EST76 sequence:

Substitution of cytosine in place of thymine at nucleotide position 444

Substitution of guanine in place of adenine at nucleotide position 673

Addition of guanine after nucleotide position 722

The first two substitutions served to remove a pair of stop codons that are present in the N-EST76 EST in reading frame 3. The last change (addition after nucleotide position 722) introduced a frameshift to connect reading frame 3 to reading frame 2 to generate a reading frame that is more homologous to full-length bZIP proteins. The DNA sequence is presented in SEQ ID NO: 22 and the protein that is expressed from the resulting construct is referred to as "N-EST76a" (SEQ ID NO:23).

Addition of Basic Region Leucine Zipper to N-EST76a

Additionally, we create a second gene in which a DNA fragment encoding a basic region leucine zipper was added to the 3' end of N-EST76a. This zipper domain is lacking in the EST for N-EST76, and is added here to create a N-EST76-derived protein that is more similar to the bZIP proteins described in the literature. Thus, a protein which is identical to N-EST76a is created except that it possesses an added zipper domain at the C-terminus. This new DNA sequence is represented in SEQ ID NO: 24 and the protein is referred to as "N-EST76b" (SEQ ID NO: 25).

These cloning strategies are summarized below.

Selection of bZIP Domain for Project

The selection of a bZIP domain for this project was carried out by selecting proteins with high homology to the translated N-EST76a sequence using the blastx search algorithm. This approach led to the identification of a rice bZIP protein with significant homology to the N-EST76a protein. The protein sequence of this rice bZIP protein (accession number BAD17130) is presented herein as SEQ ID NO: 20, with the bZIP domain represented by amino acid positions 275-357 of SEQ ID NO: 20.

The DNA sequence encoding the complete rice bZIP protein is presented in SEQ ID NO: 21, with the DNA fragment coding for the basic region leucine zipper represented by nucleotide positions 826-1074 of SEQ ID NO:21. This bZIP DNA sequence was optimized for maize codon usage and then added to the 3' end of the N-EST76a gene sequence (nucleotide position 1130 in N-EST76-H12) to create the N-EST76b gene sequence (SEQ ID NO: 24).

Example 4

Generation of Transgenic Maize Events and Nitrogen Assimilation in Maize Plants Expressing N-EST76a and N-EST76b As described in a previous Example, the plant transformation vectors pAX2433 and pAX2431 were constructed to direct overexpression of the N-EST76a and N-EST76b proteins in maize.

Each vector was introduced into an *Agrobacterium tumefaciens* strain by electroporation. This strain also contained the vector pSB1, which allows pSB1 and pAX2433 or pAX2431 to recombine in vivo to create a vector that can direct insertion of the N-EST76a or N-EST76b cassette into the maize genome. The formation of each recombinant vector (pAG2433, pAG2431) was confirmed by Southern blot hybridization of the *Agrobacterium* strain.

The *Agrobacterium* strains containing pAG2433 or pAG2431 were co-cultivated with maize embryos using methods known in the art. Following co-cultivation, the embryos were grown on selection medium. Individual events that survived selective growth in the presence of the selection agent were then moved to regeneration medium and grown to the plantlet stage using methods known in the art.

Nitrogen Assimilation in Maize Plants Expressing N-EST76a, N-EST76b

Nitrogen Assays, T0 Events

A series of assays that quantify nitrogen intermediates in plants have been developed. These assays were utilized here to analyze a total of 24 transgenic plants containing the N-EST76a gene and 6 plants containing the N-EST76b gene. Each of the plants was sampled following 4 weeks of growth in soil in a greenhouse. These plants appeared phenotypically normal. Leaf samples were processed to determine their nitrate, asparagine, glutamine, aspartic acid, glutamic acid, ammonium, total amino acid, chlorophyll and total protein levels. Included alongside in the analysis were plants that were transformed with a construct containing only the selectable marker (no N-EST76a or N-EST76b). These plants were likewise sampled at 4 weeks and are referred to as "non GOI" plants. The results of the nitrogen assays carried out on both types of plants are shown below in Table 2.

TABLE 2

Nitrogen levels, N-EST76a and N-EST76b vs. non GOI maize events, 4 weeks following transfer to soil

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 6164 | N-EST76a | 259 | 181 | 159 | 798 | 2596 | 112 | 120 | 9.18 | 0.048 |
| 6165 | N-EST76a | 557 | 288 | 204 | 546 | 3156 | 179 | 164 | 18.43 | 0.057 |
| 6166 | N-EST76a | 170 | 132 | 180 | 377 | 2921 | 122 | 163 | 15.97 | 0.040 |
| 6167 | N-EST76a | 394 | 346 | 178 | 459 | 2430 | 122 | 132 | 12.70 | 0.056 |
| 6170 | N-EST76a | 292 | 113 | 172 | 449 | 2857 | 126 | 147 | 10.09 | 0.028 |
| 6172 | N-EST76a | 259 | 160 | 198 | 326 | 2856 | 130 | 156 | 17.13 | 0.040 |
| 6173 | N-EST76a | 300 | 211 | 210 | 140 | 2024 | 179 | 152 | 17.52 | 0.069 |
| 6174 | N-EST76a | 15572 | 1604 | 208 | 470 | 2287 | 433 | 161 | 17.83 | 0.143 |
| 6175 | N-EST76a | 448 | 287 | 247 | 574 | 2542 | 247 | 166 | 15.73 | 0.078 |
| 6176 | N-EST76a | 272 | 231 | 207 | 306 | 3146 | 172 | 161 | 14.20 | 0.049 |
| 6178 | N-EST76a | 380 | 816 | 387 | 503 | 3152 | 170 | 169 | 6.71 | 0.044 |
| 6287 | N-EST76a | 772 | 126 | 372 | 290 | 2821 | 188 | 133 | 9.08 | 0.050 |
| 6288 | N-EST76a | 418 | 222 | 367 | 214 | 3010 | 114 | 153 | 10.02 | 0.036 |
| 6289 | N-EST76a | 153 | 90 | 288 | 109 | 2529 | 168 | 136 | 8.46 | 0.073 |
| 6290 | N-EST76a | 388 | 758 | 428 | 490 | 2584 | 196 | 169 | 9.78 | 0.074 |
| 6291 | N-EST76a | 241 | 112 | 277 | 697 | 1905 | 170 | 126 | 7.31 | 0.082 |
| 6292 | N-EST76a | 186 | 136 | 426 | 561 | 2259 | 158 | 144 | 14.21 | 0.066 |
| 6293 | N-EST76a | 628 | 277 | 712 | 491 | 2582 | 490 | 185 | 10.01 | 0.070 |
| 6294 | N-EST76a | 470 | 271 | 413 | 744 | 2794 | 182 | 121 | 10.96 | 0.073 |
| 6295 | N-EST76a | 197 | 169 | 484 | 263 | 2395 | 160 | 146 | 19.75 | 0.063 |
| 6296 | N-EST76a | 291 | 528 | 391 | 314 | 2537 | 153 | 130 | 13.80 | 0.046 |
| 6297 | N-EST76a | 173 | 217 | 406 | 358 | 2886 | 167 | 160 | 15.94 | 0.132 |
| 6298 | N-EST76a | 383 | 149 | 570 | 684 | 2277 | 629 | 121 | 8.41 | 0.046 |
| 6299 | N-EST76a | 524 | 364 | 439 | 191 | 1723 | 404 | 166 | 13.55 | 0.061 |
| 6155 | N-EST76b | 426 | 378 | 338 | 564 | 3587 | 142 | 180 | 14.57 | 0.045 |
| 6156 | N-EST76b | 114 | 190 | 208 | 987 | 3209 | 122 | 171 | 12.04 | 0.041 |
| 6158 | N-EST76b | 1449 | 690 | 258 | 298 | 2986 | 127 | 171 | 19.55 | 0.042 |
| 6160 | N-EST76b | 629 | 541 | 290 | 272 | 3279 | 162 | 181 | 23.69 | 0.094 |

TABLE 2-continued

Nitrogen levels, N-EST76a and N-EST76b vs. non GOI maize events, 4 weeks following transfer to soil

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 6161 | N-EST76b | 347 | 352 | 198 | 704 | 3214 | 145 | 154 | 16.00 | 0.048 |
| 6162 | N-EST76b | 483 | 226 | 183 | 581 | 2912 | 148 | 146 | 10.35 | 0.086 |
| 5986 | non-GOI | 148 | 73 | 285 | 364 | 3107 | 98 | 85 | 6.29 | 0.045 |
| 5987 | non-GOI | 652 | 32 | 280 | 544 | 2111 | 124 | 75 | 7.62 | 0.040 |
| 5988 | non-GOI | 232 | 22 | 186 | 199 | 1420 | 124 | 95 | 8.48 | 0.036 |
| 5989 | non-GOI | 123 | 55 | 256 | 354 | 2904 | 107 | 108 | 9.20 | 0.045 |
| Avg | N-EST76a (excl. 6174) | 355 | 269 | 336 | 430 | 2608 | 215 | 149 | 12.56 | 0.060 |
| Avg | N-EST76b | 575 | 396 | 246 | 568 | 3198 | 141 | 167 | 16.03 | 0.059 |
| Avg | non-GOI | 289 | 46 | 252 | 365 | 2386 | 114 | 91 | 7.90 | 0.041 |

Example 5

Generation of N-EST213 Antibodies

Synthetic peptides were generated to match the N-terminal fragment of N-EST213 ($1^{st}$ 20 amino acids of SEQ ID NO.3) and the C-terminal fragment of N-EST213 (last 20 amino acids of SEQ ID NO.3). These peptides are used to immunize rabbits using methods known in the art for the purpose of generating polyclonal antibodies against N-EST213 peptide.

Example 6

Generation of Transgenic Maize Events Using the N-EST213 Gene and Nitrogen Assimilation in Maize Plants Expressing N-EST213 (T0 Plants)

Generation of Transgenic Maize Plants that Overexpress the N-EST213 Protein

The plant transformation vector pAX2411 was constructed to direct overexpression of the N-EST213 protein in maize as described in a previous Example. The vector pAX2411 was introduced into an *Agrobacterium tumefaciens* strain by electroporation. This strain also contained the vector pSB1, which allows pSB1 and pAX2411 to recombine in vivo to create a vector that can direct insertion of the N-EST213 cassette into the maize genome. The formation of this recombinant vector (pAG2411) was confirmed by Southern blot hybridization of this *Agrobacterium* strain.

The *Agrobacterium* strain containing pAG2411 was co-cultivated with maize embryos using methods known in the art. Individual events that survived selective growth in the presence of the selection agent were then moved to regeneration medium and grown to the plantlet stage using methods known in the art.

Surprisingly, some of the plants transformed with the N-EST213 DNA were found to display an unusual phenotype. These plants were significantly shorter than non-transformed plants, with "nodal compression" present along the stalk. Seven of the 20 plants in this study exhibited this "short" phenotype. An additional 8 plants were scored as "medium" height, and an additional 4 plants were scored as "tall" height. The shorter plants developed a tassel and an ear, but both organs were sometimes undersized, and the husks were sometimes discolored or not completely formed.

Nitrogen Assimilation in Maize Plants Expressing N-EST213

A series of assays that quantify nitrogen intermediates in plants have been developed. These assays were utilized here to analyze a total of 23 transgenic plants containing the N-EST213 gene. Each of the plants was sampled following 4 weeks of growth in soil in a greenhouse. These leaf samples were processed to determine their nitrate, asparagine, glutamine, aspartic acid, glutamic acid, ammonium, total amino acid, chlorophyll and total protein levels. The results of these nitrogen assays are shown below in Table 3.

TABLE 3

Nitrogen levels, N-EST213 maize events, 4 weeks following transfer to soil

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 2811 | N-EST213 | 242 | | | | 644 | 697 | 72 | 3.10 | 0.101 |
| 2812 | N-EST213 | 158 | | | | 618 | 541 | 30 | 1.99 | 0.078 |
| 2813 | N-EST213 | 245 | 268 | 15 | | 798 | 416 | 63 | 9.10 | 0.045 |
| 2814 | N-EST213 | 296 | | 49 | 77 | 1124 | 484 | 124 | 2.40 | 0.081 |
| 2815 | N-EST213 | 202 | | | 62 | 1133 | 546 | 127 | 4.69 | 0.097 |
| 2816 | N-EST213 | 616 | | 27 | 66 | 1977 | 720 | 179 | 17.35 | 0.052 |
| 2817 | N-EST213 | 6915 | 119 | 216 | 125 | 1464 | 509 | 230 | 14.48 | 0.057 |
| 2818 | N-EST213 | 9380 | | 221 | 81 | 2413 | 829 | 228 | 14.08 | 0.119 |
| 2822 | N-EST213 | 3483 | | 109 | 50 | 1458 | 401 | 150 | 13.42 | 0.074 |
| 2823 | N-EST213 | 839 | | 79 | 229 | 2510 | 671 | 173 | 8.83 | 0.160 |
| 2824 | N-EST213 | 328 | | | | 527 | 421 | 67 | 1.63 | 0.051 |
| 2825 | N-EST213 | 162 | | | | 566 | 382 | 75 | 2.62 | 0.084 |
| 2826 | N-EST213 | 272 | | | | 394 | 367 | 50 | 1.27 | 0.119 |
| 2827 | N-EST213 | 181 | | | | 351 | 384 | 72 | 2.45 | 0.109 |
| 2828 | N-EST213 | 163 | | | | 256 | 416 | 49 | 1.78 | 0.014 |

TABLE 3-continued

Nitrogen levels, N-EST213 maize events, 4 weeks following transfer to soil

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 2829 | N-EST213 | 171 | | | | 274 | 358 | 71 | 5.25 | 0.098 |
| 2830 | N-EST213 | 185 | | 15 | | 217 | 368 | 54 | 2.20 | 0.063 |
| 2832 | N-EST213 | 205 | | | | 742 | 375 | 53 | 4.01 | 0.102 |
| 2833 | N-EST213 | 152 | | | | 354 | 383 | 53 | 1.89 | 0.057 |
| 2835 | N-EST213 | 232 | | 15 | 100 | 447 | 363 | 43 | 2.75 | 0.123 |
| 2837 | N-EST213 | 249 | | | 139 | 666 | 390 | 43 | 0.14 | 0.061 |
| 2838 | N-EST213 | 2997 | | | | 547 | 418 | 67 | | 0.113 |
| 2841 | N-EST213 | 188 | | | | 300 | 355 | 70 | 3.03 | 0.071 |
| Average | | 214 | 194 | 83 | 103 | 860 | 469 | 93 | 5 | 0.084 |
| Std Dev | | 52 | | 83 | 56 | 676 | 136 | 68 | 5.69 | 0.033 |
| CV | | 0.24 | 0.00 | 1.01 | 0.54 | 0.79 | 0.29 | 0.73 | 1.06 | 0.39 |
| # plants with positive values | 23 | 23 | 2 | 9 | 9 | 23 | 23 | 23 | 22 | 23 |
| | | 2816 to 2823, 2838 excluded | | | | | | | | |

Control samples were also generated from transgenic maize plants that contained the selectable marker cassette only (no N-EST213). These samples were likewise sampled at 4 weeks, and the nitrogen levels were determined. These data are shown in Table 4.

TABLE 4

Nitrogen levels, non-GOI plants, 4 weeks following planting

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 2760 | non GOI | 24939 | | 257 | 92 | 1423 | 551 | 151 | 16.77 | 0.022 |
| 2761 | non GOI | 7159 | | 196 | 74 | 1151 | 607 | 146 | 17.59 | 0.038 |
| 2762 | non GOI | 1625 | 146 | 225 | 58 | 1177 | 445 | 141 | 13.33 | 0.036 |
| 2763 | non GOI | 4421 | | 197 | 119 | 1172 | 487 | 111 | 11.08 | 0.038 |
| 2765 | non GOI | 1901 | | 131 | 69 | 874 | 366 | 92 | 9.10 | 0.032 |
| 2766 | non-GOI | 233 | | 14 | | 184 | 352 | 56 | 5.33 | 0.085 |
| 2768 | non-GOI | 210 | | 9 | | 256 | 346 | 64 | 5.54 | 0.062 |
| 2769 | non-GOI | 245 | | 17 | | 249 | 481 | 56 | 4.08 | 0.055 |
| Average | | 229 | 146 | 131 | 83 | 811 | 454 | 102 | 10 | 0.046 |
| Std Dev | | 18 | | 104 | 24 | 503 | 96 | 41 | 5 | 0.020 |
| CV | | 0.08 | | 0.79 | 0.29 | 0.62 | 0.21 | 0.40 | 0.51 | 0.44 |
| # plants with positive values | 8 | 3 | 1 | 8 | 5 | 8 | 8 | 8 | 8 | 8 |

Example 7

Generation of Transgenic Maize Events and Nitrogen Assimilation in Maize Plants Expressing N-EST45 (T0 and T1 Plants)

Generation of Transgenic Maize Plants that Overexpress the N-EST45 Protein

As described in the previous Example, the plant transformation vector pAX3404 was constructed to direct overexpression of the N-EST45 protein in maize.

The vector pAX3404 was introduced into an *Agrobacterium tumefaciens* strain by electroporation. This strain also contained the vector pSB1, which allows pSB1 and pAX3404 to recombine in vivo to create a vector that can direct insertion of the N-EST45 cassette into the maize genome. The formation of this recombinant vector (pAG3404) was confirmed by Southern blot hybridization of this *Agrobacterium* strain.

The *Agrobacterium* strain containing pAG3404 was co-cultivated with maize embryos using methods known in the art. Following co-cultivation, the embryos were grown on selection medium. Individual events that survived selective growth in the presence of the selection agent were then moved to regeneration medium and grown to the plantlet stage using methods known in the art. These plants appeared phenotypically normal.

Nitrogen Assimilation in Maize Plants Expressing N-EST45

Nitrogen Assays, T0 Events

A series of assays that quantify nitrogen intermediates in plants have been developed. These assays were utilized here to analyze a total of 16 transgenic plants containing the N-EST45 gene. Each of the plants was sampled following 4 weeks of growth in soil in a greenhouse. These leaf samples were processed to determine their nitrate, asparagine, glutamine, aspartic acid, glutamic acid, ammonium, total amino acid, chlorophyll and total protein levels. Included alongside in the analysis were plants that were transformed with a construct containing only the selectable marker (no N-EST45). These plants were likewise sampled at 4 weeks and are referred to as "non GOI" plants. The results of the nitrogen assays carried out on both types of plants are shown below in Table 5.

seed set and seed harvest, dried seeds from these crosses were germinated in soil. Approximately 2 weeks after planting, segregants containing the N-EST45 gene (or selectable marker gene in non-GOI plants) were identified and grown

TABLE 5

Nitrogen levels, N-EST45 vs. non GOI maize events, 4 weeks following transfer to soil

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 3751 | N-EST45 | 216 | 178 | 155 | 102 | 1383 | 403 | 84 | 1.30 | 0.074 |
| 3752 | N-EST45 | 251 | | 129 | 317 | 1485 | 407 | 104 | 1.34 | 0.092 |
| 3754 | N-EST45 | 457 | 446 | 402 | 557 | 3378 | 768 | 240 | 2.59 | 0.104 |
| 3755 | N-EST45 | 293 | 416 | 321 | 645 | 2143 | 484 | 144 | 1.81 | 0.065 |
| 3759 | N-EST45 | 656 | | 211 | 379 | 2068 | 413 | 135 | 1.73 | 0.051 |
| 3760 | N-EST45 | 7172 | 221 | 238 | 661 | 2421 | 627 | 184 | 1.88 | 0.092 |
| 3762 | N-EST45 | 809 | | 150 | 273 | 1752 | 369 | 128 | 1.24 | 0.090 |
| 3764 | N-EST45 | 233 | | 108 | 203 | 1919 | 301 | 106 | 0.86 | 0.073 |
| 3765 | N-EST45 | 598 | | 121 | 284 | 1409 | 437 | 112 | 1.47 | 0.137 |
| 3768 | N-EST45 | 271 | | 118 | 321 | 1430 | 321 | 116 | 1.14 | 0.052 |
| 3771 | N-EST45 | 480 | 117 | 189 | 462 | 1221 | 525 | 129 | 1.89 | 0.183 |
| 3772 | N-EST45 | 565 | 231 | 167 | 395 | 2083 | 410 | 111 | 1.05 | 0.076 |
| 3773 | N-EST45 | 659 | | 105 | 263 | 1634 | 445 | 101 | 1.63 | 0.088 |
| 3779 | N-EST45 | 533 | 96 | 138 | 354 | 1745 | 397 | 126 | 0.99 | 0.095 |
| 3781 | N-EST45 | 500 | 109 | 144 | 286 | 1477 | 490 | 137 | 1.28 | 0.094 |
| 3784 | N-EST45 | 1209 | 90 | 144 | 228 | 1446 | 424 | 135 | 1.11 | 0.089 |
| 2771 (non-GOI) | non-GOI | 354 | | 224 | 132 | 1065 | 506 | 117 | 0.88 | 0.073 |
| 2773 (non-GOI) | non-GOI | 183 | | 188 | 209 | 1040 | 365 | 109 | 1.27 | 0.044 |
| 2774 (non-GOI) | non-GOI | 135 | | 223 | 158 | 629 | 470 | 102 | 1.38 | 0.045 |
| Average (GOI) | | 466 | 212 | 177 | 358 | 1812 | 451 | 131 | 1.46 | 0.091 |
| Std Dev | | 187 | 135 | 82 | 156 | 537 | 115 | 37 | 0.44 | 0.032 |
| CV | | 0.40 3760, 3784 excluded | 0.64 | 0.46 | 0.43 | 0.30 | 0.25 | 0.28 | 0.30 | 0.35 |

Nitrogen Assays, T1 Events

The nitrogen levels present in the T0 N-EST45 maize events were examined and several plants were selected for characterization as T1 plants. Events ("plant #") 3755, 3759, 3760, 3765, 3773 and 3781 were chosen. Non-GOI events 3822 and 3828 were selected as negative controls. To generate T1 plants, pollen was collected from each of the T0 events and used to pollinate ears on Hi-II (A188×B73) plants. Following until 4 weeks of age. These plants appeared phenotypically normal. Leaf samples were taken from these events at 4 weeks and entered into the same nitrogen testing scheme utilized for the T0 plants (nitrate, asparagine, glutamine, aspartic acid, glutamic acid, ammonium, total amino acid, chlorophyll and total protein). The results of these nitrogen assays are shown in Table 6.

TABLE 6

Nitrogen levels, T1 plants, N-EST45 vs. non-GOI events

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 3751 | N-EST45 | 216 | 178 | 155 | 102 | 1383 | 403 | 84 | 1.30 | 0.074 |
| 3752 | N-EST45 | 251 | | 129 | 317 | 1485 | 407 | 104 | 1.34 | 0.092 |
| 3754 | N-EST45 | 457 | 446 | 402 | 557 | 3378 | 768 | 240 | 2.59 | 0.104 |
| 3755 | N-EST45 | 293 | 416 | 321 | 645 | 2143 | 484 | 144 | 1.81 | 0.065 |
| 3759 | N-EST45 | 656 | | 211 | 379 | 2068 | 413 | 135 | 1.73 | 0.051 |
| 3760 | N-EST45 | 7172 | 221 | 238 | 661 | 2421 | 627 | 184 | 1.88 | 0.092 |
| 3762 | N-EST45 | 809 | | 150 | 273 | 1752 | 369 | 128 | 1.24 | 0.090 |
| 3764 | N-EST45 | 233 | | 108 | 203 | 1919 | 301 | 106 | 0.86 | 0.073 |
| 3765 | N-EST45 | 598 | | 121 | 284 | 1409 | 437 | 112 | 1.47 | 0.137 |
| 3768 | N-EST45 | 271 | | 118 | 321 | 1430 | 321 | 116 | 1.14 | 0.052 |
| 3771 | N-EST45 | 480 | 117 | 189 | 462 | 1221 | 525 | 129 | 1.89 | 0.183 |
| 3772 | N-EST45 | 565 | 231 | 167 | 395 | 2083 | 410 | 111 | 1.05 | 0.076 |
| 3773 | N-EST45 | 659 | | 105 | 263 | 1634 | 445 | 101 | 1.63 | 0.088 |
| 3779 | N-EST45 | 533 | 96 | 138 | 354 | 1745 | 397 | 126 | 0.99 | 0.095 |
| 3781 | N-EST45 | 500 | 109 | 144 | 286 | 1477 | 490 | 137 | 1.28 | 0.094 |
| 3784 | N-EST45 | 1209 | 90 | 144 | 228 | 1446 | 424 | 135 | 1.11 | 0.089 |
| 2771 (non-GOI) | non-GOI | 354 | | 224 | 132 | 1065 | 506 | 117 | 0.88 | 0.073 |

TABLE 6-continued

Nitrogen levels, T1 plants, N-EST45 vs. non-GOI events

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 2773 (non-GOI) | non-GOI | 183 | | 188 | 209 | 1040 | 365 | 109 | 1.27 | 0.044 |
| 2774 (non-GOI) | non-GOI | 135 | | 223 | 158 | 629 | 470 | 102 | 1.38 | 0.045 |
| Average (GOI) | | 466* | 212 | 177 | 358 | 1812 | 451 | 131 | 1.46 | 0.091 |
| Std Dev | | 187* | 135 | 82 | 156 | 537 | 115 | 37 | 0.44 | 0.032 |
| CV | | 0.40* | 0.64 | 0.46 | 0.43 | 0.30 | 0.25 | 0.28 | 0.30 | 0.35 |
| Average (non GOI) | | 224 | undet | 211 | 166 | 911 | 447 | 110 | 1.17 | 0.054 |
| Std Dev | | 115 | | 20 | 39 | 245 | 73 | 8 | 0.26 | 0.017 |
| CV | | 0.52 | | 0.10 | 0.23 | 0.27 | 0.16 | 0.07 | 0.22 | 0.31 |

*3760, 3784 excluded

Example 8

Generation of Transgenic Maize Events and Nitrogen Assimilation in Maize Plants Expressing N-EST61

As described in the previous Example, the plant transformation vector pAX2422 was constructed to direct overexpression of the N-EST61 protein in maize.

The vector pAX2422 was introduced into an *Agrobacterium tumefaciens* strain by electroporation. This strain also contained the vector pSB1, which allows pSB1 and pAX2422 to recombine in vivo to create a vector that can direct insertion of the N-EST61 cassette into the maize genome. The formation of this recombinant vector (pAG2422) was confirmed by Southern blot hybridization of this *Agrobacterium* strain.

The *Agrobacterium* strain containing pAG2422 was co-cultivated with maize embryos using methods known in the art. Following co-cultivation, the embryos were grown on selection medium. Individual events that survived selective growth in the presence of the selection agent were then moved to regeneration medium and grown to the plantlet stage using methods known in the art. These plants appeared phenotypically normal.

Nitrogen Assimilation in Maize Plants Expressing N-EST61

Nitrogen Assays, T0 Events

A series of assays that quantify nitrogen intermediates in plants have been developed. These assays were utilized here to analyze a total of 8 transgenic plants containing the N-EST61 gene. Each of the plants was sampled following 4 weeks of growth in soil in a greenhouse. These leaf samples were processed to determine their nitrate, asparagine, glutamine, aspartic acid, glutamic acid, ammonium, total amino acid, chlorophyll and total protein levels. Included alongside in the analysis were plants that were transformed with a construct containing only the selectable marker (no N-EST61). These plants were likewise sampled at 4 weeks and are referred to as "non GOI" plants. The results of the nitrogen assays carried out on both types of plants are shown below in Table 7.

TABLE 7

Nitrogen levels, N-EST61 vs. non GOI maize events, 4 weeks following transfer to soil

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 5629 | N-EST61 | 205 | 79 | 267 | 287 | 1954 | 204 | 71 | 25.29 | 0.095 |
| 5630 | N-EST61 | 790 | 59 | 223 | 976 | 2371 | 202 | 98 | 18.91 | 0.092 |
| 5632 | N-EST61 | 222 | 144 | 266 | 651 | 2630 | 292 | 100 | 12.41 | 0.076 |
| 5633 | N-EST61 | 193 | 64 | 314 | 1132 | 1738 | 387 | 80 | 8.88 | 0.067 |
| 5635 | N-EST61 | 383 | 54 | 202 | 574 | 1431 | 248 | 72 | 8.37 | 0.080 |
| 5636 | N-EST61 | 449 | 67 | 349 | 594 | 1545 | 402 | 87 | 9.93 | 0.042 |
| 5637 | N-EST61 | 354 | 292 | 368 | 389 | 2519 | 244 | 116 | 20.12 | 0.127 |
| 5638 | N-EST61 | 1477 | 37 | 292 | 835 | 1360 | 224 | 84 | 8.51 | 0.051 |
| 5983 | non-GOI | 345 | 61 | 264 | 71 | 1435 | 215 | 296 | 7.98 | 0.107 |
| 5984 | non-GOI | 213 | 155 | 850 | 398 | 3670 | 117 | 355 | 14.11 | 0.081 |
| 5985 | non-GOI | 212 | 73 | 199 | 566 | 2039 | 182 | 294 | 2.67 | 0.058 |
| Average (N-EST61) | | 509 | 100 | 285 | 680 | 1943 | 275 | 89 | 14.05 | 0.079 |
| Average (non-GOI) | | 256 | 96 | 438 | 345 | 2381 | 171 | 315 | 8.25 | 0.082 |

Example 9

Generation of Transgenic Maize Events and Nitrogen Assimilation in Maize Plants Expressing N-EST15

As described in the previous Example, the plant transformation vector pAX2437 was constructed to direct overexpression of the N-EST15 protein in maize.

The vector pAX2437 was introduced into an *Agrobacterium tumefaciens* strain by electroporation. This strain also contained the vector pSB1, which allows pSB1 and pAX2437 to recombine in vivo to create a vector that can direct insertion of the N-EST15 cassette into the maize genome. The formation of this recombinant vector (pAG2437) was confirmed by Southern blot hybridization of this *Agrobacterium* strain.

The *Agrobacterium* strain containing pAG2437 was co-cultivated with maize embryos using methods known in the art. Following co-cultivation, the embryos were grown on selection medium. Individual events that survived selective growth in the presence of the selection agent were then moved to regeneration medium and grown to the plantlet stage using methods known in the art. These plants appeared phenotypically normal.

Nitrogen Assimilation in Maize Plants Expressing N-EST15

Nitrogen Assays, T0 Events

A series of assays that quantify nitrogen intermediates in plants have been developed. These assays were utilized here to analyze a total of 8 transgenic plants containing the N-EST15 gene. Each of the plants was sampled following 4 weeks of growth in soil in a greenhouse. These leaf samples were processed to determine their nitrate, asparagine, glutamine, aspartic acid, glutamic acid, ammonium, total amino acid, chlorophyll and total protein levels. Included alongside in the analysis were plants that were transformed with a construct containing only the selectable marker (no N-EST15). These plants were likewise sampled at 4 weeks and are referred to as "non GOI" plants. The results of the nitrogen assays carried out on both types of plants are shown below in Table 8.

The vector pAX2439 was introduced into an *Agrobacterium tumefaciens* strain by electroporation. This strain also contained the vector pSB1, which allows pSB1 and pAX2439 to recombine in vivo to create a vector that can direct insertion of the N-EST28 cassette into the maize genome. The formation of this recombinant vector (pAG2439) was confirmed by Southern blot hybridization of this *Agrobacterium* strain.

The *Agrobacterium* strain containing pAG2439 was co-cultivated with maize embryos using methods known in the art. Following co-cultivation, the embryos were grown on selection medium. Individual events that survived selective growth in the presence of the selection agent were then moved to regeneration medium and grown to the plantlet stage using methods known in the art. These plants appeared phenotypically normal.

Nitrogen Assimilation in Maize Plants Expressing N-EST28

Nitrogen Assays, T0 Events

A series of assays that quantify nitrogen intermediates in plants have been developed. These assays were utilized here to analyze a total of 5 transgenic plants containing the N-EST28 gene. Each of the plants was sampled following 4 weeks of growth in soil in a greenhouse. These leaf samples were processed to determine their nitrate, asparagine, glutamine, aspartic acid, glutamic acid, ammonium, total

TABLE 8

Nitrogen levels, N-EST15 vs. non GOI maize events, 4 weeks following transfer to soil

| Plant # | GOI | Nitrate (µg/g) | Asparagine (µg/g) | Glutamine (µg/g) | Aspartic Acid (µg/g) | Glutamic Acid (µg/g) | Ammonium (µg/g) | Total Amino Acids (mg/g) | Total Protein (mg/g) | Total Chlorophyll (a + b) (mg/g) |
|---|---|---|---|---|---|---|---|---|---|---|
| 5923 | N-EST15 | 111 | 245 | 267 | 1036 | 3244 | 142 | 321 | 10.41 | 0.074 |
| 5924 | N-EST15 | 401 | 470 | 330 | 685 | 3271 | 142 | 349 | 8.65 | 0.056 |
| 5926 | N-EST15 | 554 | 65 | 202 | 308 | 2376 | 183 | 327 | 9.22 | 0.072 |
| 5929 | N-EST15 | 591 | 256 | 238 | 1551 | 2562 | 168 | 338 | 9.98 | 0.053 |
| 5930 | N-EST15 | 1873 | 909 | 477 | 3059 | 2495 | 174 | 458 | 12.98 | 0.065 |
| 5931 | N-EST15 | 2275 | 382 | 268 | 1023 | 3590 | 196 | 357 | 6.42 | 0.073 |
| 5932* | N-EST15 | 414 | 1107 | 739 | 1751 | 4049 | 430 | 683 | 16.79 | 0.125 |
| 5934 | N-EST15 | 272 | 290 | 293 | 863 | 2306 | 163 | 312 | 7.37 | 0.047 |
| 5983 | non-GOI | 345 | 61 | 264 | 71 | 1435 | 215 | 296 | 7.98 | 0.107 |
| 5984 | non-GOI | 213 | 155 | 850 | 398 | 3670 | 117 | 355 | 14.11 | 0.081 |
| 5985 | non-GOI | 212 | 73 | 199 | 566 | 2039 | 182 | 294 | 2.67 | 0.058 |
| Average (N-EST15) | | 811 | 465 | 352 | 1285 | 2987 | 200 | 393 | 10.23 | 0.071 |
| Average (non-GOI) | | 256 | 96 | 438 | 345 | 2381 | 171 | 315 | 8 | 0.082 |

*5932 water content measured higher than others (93% vs. avg of 85%); also extremely fibrous and easily shredded Example 9

Generation of Transgenic Maize Events and Nitrogen Assimilation in Maize Plants Expressing N-EST28

As described in the previous Example, the plant transformation vector pAX2439 was constructed to direct overexpression of the N-EST28 protein in maize.

amino acid, chlorophyll and total protein levels. Included alongside in the analysis were plants that were transformed with a construct containing only the selectable marker (no N-EST28). These plants were likewise sampled at 4 weeks and are referred to as "non GOI" plants. The results of the nitrogen assays carried out on both types of plants are shown below in Table 9.

TABLE 9

Nitrogen levels, N-EST28 vs. non GOI maize events, 4 weeks following transfer to soil

| Plant # | GOI | Nitrate (μg/g) | Asparagine (μg/g) | Glutamine (μg/g) | Aspartic Acid (μg/g) | Glutamic Acid (μg/g) | Ammonium (μg/g) | Total Amino Acids (mg/g) | Total Protein (mg/g) | Total Chlorophyll (a + b) (mg/g) |
|---|---|---|---|---|---|---|---|---|---|---|
| 6179 | N-EST28 | 230 | 393 | 385 | 458 | 3209 | 116 | 137 | 15.22 | 0.026 |
| 6180 | N-EST28 | 282 | 392 | 415 | 151 | 3613 | 126 | 175 | 22.09 | 0.074 |
| 6182 | N-EST28 | 271 | 132 | 248 | 340 | 2722 | 133 | 103 | 8.77 | 0.050 |
| 6183 | N-EST28 | 244 | 177 | 291 | 1098 | 2976 | 122 | 113 | 9.59 | 0.088 |
| 6184 | N-EST28 | 183 | 253 | 325 | 496 | 3143 | 123 | 119 | 11.40 | 0.050 |
| 5986 | non-GOI | 148 | 73 | 285 | 364 | 3107 | 98 | 85 | 6.29 | 0.045 |
| 5987 | non-GOI | 652 | 32 | 280 | 544 | 2111 | 124 | 75 | 7.62 | 0.040 |
| 5988 | non-GOI | 232 | 22 | 186 | 199 | 1420 | 124 | 95 | 8.48 | 0.036 |
| 5989 | non-GOI | 123 | 55 | 256 | 354 | 2904 | 107 | 108 | 9.20 | 0.045 |
| Avg | N-EST28 | 242 | 270 | 333 | 509 | 3133 | 124 | 129 | 13.41 | 0.057 |
| Avg | non-GOI | 289 | 46 | 252 | 365 | 2386 | 114 | 91 | 7.90 | 0.041 |

Example 11

Generation of Transgenic Maize Events and Nitrogen Assimilation in Maize Plants Expressing N-EST88, N-EST42, N-EST31, N-EST264

As described in the previous Example, the plant transformation vectors pAX2424 (N-EST88), pAX2435 (N-EST42), pAX2441 (N-EST31) and pAX2437 (N-EST264) were constructed to direct overexpression of the N-EST88, N-EST42, N-EST31 and N-EST264 proteins in maize.

Each vector was introduced into an *Agrobacterium tumefaciens* strain by electroporation. This strain also contained the vector pSB1, which allows pSB1 and pAX2424, pAX2435, pAX2441 or pAX2437 to recombine in vivo to create a vector that can direct insertion of the N-EST28 cassette into the maize genome. The formation of these recombinant vectors (pAG2424, pAG2435, pAG2441 or pAG2437) was confirmed by Southern blot hybridization of this *Agrobacterium* strain.

The *Agrobacterium* strains containing pAG2424, pAG2435, pAG2441 or pAG2437 were co-cultivated with maize embryos using methods known in the art. Following co-cultivation, the embryos were grown on selection medium. Individual events that survived selective growth in the presence of the selection agent were then moved to regeneration medium and grown to the plantlet stage using methods known in the art. These plants appeared phenotypically normal.

Example 12

Generation of Plasmids to Direct Overexpression of the N-EST43, N-EST13A, N-EST13E or N-EST55C Proteins in Transgenic Maize Events As described in the previous Example, the plant transformation vectors pAX2443 (N-EST43), pAX2454 (N-EST13A), pAX2457 (N-EST13E) and pAX2460 (N-EST55C) were constructed to direct overexpression of the N-EST43, N-EST13A, N-EST13E or N-EST55C proteins in maize.

Each vector was introduced into an *Agrobacterium tumefaciens* strain by electroporation. This strain also contained the vector pSB1, which allows pSB1 and pAX2443, pAX2454, pAX2457 or pAX2460 to recombine in vivo to create a vector that can direct insertion of the N-EST43, N-EST13A, N-EST13E or N-EST55C cassette into the maize genome. The formation of these recombinant vectors (pAG2443, pAG2454, pAG2457 or pAG2460) was confirmed by Southern blot hybridization of this *Agrobacterium* strain.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto. Those skilled in the art who have the disclosure before them will be able to make modifications and variations therein without departing from the scope of the invention.

SEQUENCE LISTING

SEQ ID NO: 1
TCGACTGGAGCACGAGGACACTGACATGGACTGAAGGAGTAGAAAATCACCTAGCTAGAAAGGAGAGCAC
CGAGCGCTGCACCACTACTGCTGATATGAGCACCTGAACCTTCTGGGCAACCACATCGTCCCTGCCCCTG
ATCATCCGCAGCAGCC**ATGGCGCAGCAGCAGGAGAAGAAGCAGCAGCAGAGGGGGAAGCTGCAGAGGGTG
CTAAGGGAGCAGAAGGCTCGGCTCTACATCATCCGCCGATGCGCGTCATGCTCCTCTGCTGGAGTGACTG**
ATCCATCTCAAGCATGCATGATAAACCTGTGCTCTTTTTTTTTCCTTCTGTTTTTTCCCCTCTTTTTCCC
ATCCTTTTCACCTTGCCACTTTGGTGGGCG

SEQ ID NO: 2
ATGGCGCAGCAGCAGGAGAAGAAGCAGCAGCAGAGGGGGAAGCTGCAGAGGGTGCTAAGGGAGCAGAAGG
CTCGGCTCTACATCATCCGCCGATGCGCGTCATGCTCCTCTGCTGGAGTGACTGA

SEQ ID NO: 3
MAQQQEKKQQQRGKLQRVLREQKARLYIIRRCVVMLLCWSD

SEQ ID NO.: 4
ATGTGCATTGCTGCATGGATTTGGCAGGCTCACCCTGTGCACCAACTCCTCCTGCTTCTCAACAGAGATG
AGTTCCACAGCAGGCCTACAAAAGCAGTAGGATGGTGGGGTGAAGGCTCAAAGAAGATCCTTGGTGGCAG
GGATGTGCTTGGTGGAGGAACATGGATGGGGTGCACCAAGGATGGAAGGCTTGCCTTCCTGACCAATGTG
CTTGAACCAGATGCCATGCCCGGTGCACGGACTAGGGGAGATCTGCCTCTCAAATTCCTGCAGAGCAACA
AGAGCCCACTCGAAGTTGCAACTGAAGTGGCAGAAGAAGCTGATGAATACAATGGCTTCAACCTCATACT
AGCTGATCTAACAACAAATATCATGGTTTATGTGTCAAACCGGCCTAAGGGTCAGCCTGCAACAATTCAA
CTCGTGTCACCAGGACTCCATGTGCTGTCCAATGCAAGGCTAGATAGCCCTTGGCAGAAGGCAATTCTCC
TCGGTAAAAACTTCAGGGAGCTTCTTAGGGAGCATGGTGCTGATGAGGTTGAAGTGAAGGATATAGTTGA
GAGGCTAATGACTGACACCACAAAGGCTGACAAAGATAGACTGCCAAACACTGGTTGTGATCCCAACTGG
GAGCATGGTCTGAGCTCCATCTTCATTGAGGTGCAAACTGACCAAGGGCCCTATGGGACACGGAGCACAG
CCGTTTTATCAGTGAACTATGATGGCGAAGCTAGCTTGTACGAGAAGTATCTTGAGAGTGGTATATGGAA
GGATCACACAGTGAGTTACCAGATAGAGTAG

SEQ ID NO: 5
MCIAAWIWQA HPVHQLLLLL NRDEFHSRPT KAVGWWGEGS KKILGGRDVL GGGTWMGCTK
DGRLAFLTNV LEPDAMPGAR TRGDLPLKFL QSNKSPLEVA TEVAEEADEY NGFNLILADL
TTNIMVYVSN RPKGQPATIQ LVSPGLHVLS NARLDSPWQK AILLGKNFRE LLREHGADEV
EVKDIVERLM TDTTKADKDR LPNTGCDPNW EHGLSSIFIE VQTDQGPYGT RSTAVLSVNY
DGEASLYEKY LESGIWKDHT VSYQIE

SEQ ID NO: 6
ATTCCCGTCTTACCTAGCGCTAGGGTTAGTACGCGTCCACGGCGACGACCTCTGCGCGGAGTGTGCTCCG
ATTGGCTGGCCTCCTCGATCCTCCTTCCCGCGAACGCACGCGCGCGCGAGGGAGAGGTTGAGACTTGAGA
GATAGACGAAAGACGAAACAAGGGAAGGAGACGCCGTGCTCGCCTATTGGCCGCCGCCTCCGCTCCTTCG
CGCCCAATGGCTTCTGCAGCATATCAATATATGCAGCATAGCAGTACTCAGACCCTTACTACGCAGGCG
TTGTTGCTCCCTATGGAAGTCAAGATGTGTGTCCGAGGAGCCTGTCTATGTGAACGCCAAGCAGTACCGC
GGCATTCTAAGACGGCGGCAGTCACGTGCCAAGGCCGAGCTTGAGAGAAAGCGCTGGTCAAAGCAAGAAA
GCCGTATCTTCACGAGTCCCCGTCATCAGCACGCGATGACGAGGAGGGCGAGAGGGAACGGTGGACGCTT
CCTAAACACGAAGAAGAGTGACCGTGTCCCTCCTGATGACTTGATACAGCTACGACGACACAACGAGGCT
TGAAGAGGTAGCGGTCTGGCTGGCATCCTAGAGCAGCGGTTTCTGTCCACAGGCACGTGCATCTGAGACC
GGATCCGTAGCTCCACTCCACAGCATATGCGCAGCCCATCCATCTCGTGCACACTTG

SEQ ID NO: 7
ATGCAGCATAGCAGTACTCAGACCCTTACTACGCAGGCGTTGTTGCTCCCTATGGAAGTCAAGATGTGTG
TCCGAGGAGCCTGTCTATGTGAACGCCAAGCAGTACCGCGGCATTCTAAGACGGCGGCAGTCACGTGCCA
AGGCCGAGCTGA

SEQ ID NO: 8
MQHSSTQTLT TQALLLPMEV KMCVRGACLC ERQAVPRHSK TAAVTCQGRA

SEQ ID NO: 9
TTGAGAGATAGACGAAAGACGAAACAAGGGAAGGAGACGCCGTGCTCGCCTATTGGCCGCCGCCTCCGCT
CCTTCGCGCCCAATGGCTTCTGCAGCATATCAATATCATGCAGCATAGCAGTACTCAGACCCTTACTACG
CAGGCGTTGTTGCTCCCTATGGAAGTCAAGATGTGTGTCCGAGGAGCCTGTCTATGTGAACGCCAAGCAG
TACCGCGGCATTCTAAGACGGCGGCAGTCACGTGCCAAGGCCGAGCTTGAGAGAAAGCGCTGGTCAAAGC
AAGAAAGCCGTATCTTCACGAGTCCCCGTCATCAGCACGCGATGACGAGGAGGGCGAGAGGGAACGGTGG
ACGCTTCCTAAACACGAAGAAGAGTGACCGTGTCCCTCCTGATGACTTGATACAGCTACGACGACACAAC
GAGGCTTGA

SEQ ID NO: 10
LRDRRKTKQG KETPCSPIGR RLRSFAPNGF CSISISCSIA VLRPLLRRRC CSLWKSRCVS
EEPVYVNAKQ YRGILRRRQS RAKAELERKR WSKQESRIFT SPRHQHAMTR RARGNGGRFL
NTKKSDRVPP DDLIQLRRHN EA

SEQ ID NO: 11
ATGACTGCTCACCAGACTTGCTGCGATGATGCCGTTGCCGCCGGCACTGCACCGGCTGCCAGGAGGAGGC
GCCTCAAATTGACGAGGCCGTCGGCCTCGCTCTTGATGGCGAGGAAGCTAAGGAAGAAGGCTGCCGGCAG
CAAACGCCCAAGGGCGGCAGCGTCGAGGAAGCGCGCGATGGCGATCAGGAGGAAGATGGAAGCGCTGAGG
CTGCTCGTGCCACTCTGCGGCCGAGACAACGGCTCGGTGACCGGTGGGCGGTCGAACGACTGGACGAGC
TCCTCATGCACGCCGCCGGGTACATCCTGCGCCTCCAGATGCAGGTCAGAGTGATGCAGCTTATGGTCCA
TGCACTAAATGACCGGCCCGAGGATTAA

SEQ ID NO: 12
MTAHQTCCDDAVAAGTAPAARRRRLKLTRPSASLLMARKLRKKAAGSKRPRAAASRKRAMAIRRKMEALR
LLVPLCGRDNGSVTGGAVERLDELLMHAAGYILRLQMQVRVMQLMVHALNDRPED

SEQ ID NO: 13
ATGTCGGCGGCGCTCGCGGTGACGGACGAGGTGGCCCTGCCGATCCGGGCGGTGGGGGATCTAGCGGCCG
CCGCCGAGGTCTCGCGGGAGGAGGTCGCCGTCATCACCCAGTGCGCGGCGCTCGGTGGGAAGTTGCCTTT
TGAAGATGCATCAGTTGGTGCGGTTCTTGCAGTCATTAAAAACGTGGAAAGCTTGAGGGAGCAATTGGTT
GCTGAAATCAGGCGGGTGCTGAAAGCTGGTGGAAGAGTATTGGTGCAGAGCCCTGCACCCTCATCCAGTC
AGAAGCCGAACACTGATATTGAGCGCAAGTTACTGATGGGTGGATTTGCTGAAGTGCAATCTTCTGCTGC
AAGCTCGCAGGATAGCGTGCAATCTGTTACAGTTAAGGCAAAGAAGGCTAGCTGGAGCATGGGCTCTTCT
TTTCCCCTTAAGAAAACAACAAAAGCCCTTCCCAAGATTCAAATTGACGACGACTCTGATCTGATTGATG

```
-continued
AAGACAGTCTCTTGACTGAGGAGGACCTGAAGAAACCACAACTTCCAGTTGTTGGGGACTGTGAGGTGGG
GGCAGCAAAGAAAGCATGCAAGAACTGTACTTGTGGCAGGGCTGAGGCCGAGGAGAAGGTTGGGAAGCTG
GAGCTCACTGCGGAGCAGATCAATAACCCTCAGTCAGCTTGTGGCAGTTGTGGGTTGGGTGATGCCTTCC
GCTGTGAACCTGTCCCTACAGAGGTCTTCCACCATTCAAGCCTGGCGAGAAGGTTTCCTTGTCTGGCAA
CTTCCTTGCTGCTGACATATGA SEQ ID NO: 14
MSAALAVTDEVALPIRAVGDLAAAAEVSREEVAVITQCAALGGKLPFEDASVGAVLAVIKNVESLREQLV
AEIRRVLKAGGRVLVQSPAPSSSQKPNTDIERKLLMGGFAEVQSSAASSQDSVQSVTVKAKKASWSMGSS
FPLKKTTKALPKIQIDDDSDLIDEDSLLTEEDLKKPQLPVVGDCEVGAAKKACKNCTCGRAEAEEKVGKL
ELTAEQINNPQSACGSCGLGDAFRCGTCPYRGLPPFKPGEKVSLSGNFLAADI SEQ ID NO: 15
ATGGCGATGCAGACGGGGGTCGCGACCTCCAAGGTCCTCATCCTCGTCGGTGCAGGGATGACGGGCTCGA
TCCTGCTGCGGAATGGCCGCTTATCTGATGTGTTGGGAGAACTCCAGGAGATTATGAAGGGTGTAAATCA
AGGAACTTCTTCGGGTCCCTATGACATTGCACTTATTCAAGCTCAGATTCGGAATTTAGCGCAAGAAGTC
AGAGATTTGACATTGTCAAAGCCCATTACCATACTGAATGGCAAATCTGACTCGGGAGGCAGTTTATCAT
CCTACATACTGCCAGCAGCAGCAGTTGGAGCAATGGGTTATTGCTATGTGGTGGAAGGGGTTGTCTCT
CTCCAGATGTCATGTTTGTCACAAAACACAACATGGCAAATGCTGTTCAGAGCATGTCAAAGCAGTTGGAG
CAAGTTTCATCAGCACTAGCTGCAACAAAAAGACATCTAACTCAACGGCTTGAGAATTTGGATGGCAAAA
TGGATGAACAAGTAGAGGTCTCCAAAGCTATTAGAAATGAGGTCAATGATGTTAAAGATGACCTGTCTCA
AATTGGATTTGATGTCGAATCAATTCAGAAAATGGTTGCTGGATTGGAGGGAAAGATCGAGTTACTTGAG
AACAAACAGGACGTGGCTAATACTGGTATCTGGTATCTCTGCCAAGTAGCAGGCGGTTTAAAAGATGGAA
TAAACACCAGGTTTTTCCAGGAAACCAGTGAGAAGCTGAAGCTCTCACATTCAGCTCAACCTGAAAACAA
GCCAGTGAAGGGGCTTGAATTTTTTCGGAAAGCACCATGGAACAGAAAGTAGCTGACTCCAAACCAATT
GCGGTGACAGTTGACGCTGAGAAGCCTGAGAAACCGCTGCTGTAATGGGCACCACAGTGCACAGGTCTA
TCAGGTTCTCATATCGGAAGGCAGGCCTTGCTTTGTGA SEQ ID NO: 16
MAMQTGVATS KVLILVGAGM TGSILLRNGR LSDVLGELQE IMKGVNQGTS SGPYDIALIQ
AQIRNLAQEV RDLTLSKPIT ILNGKSDSGG SLSSYILPAA AVGAMGYCYM WWKGLSLSDV
MFVTKHNMAN AVQSMSKQLE QVSSALAATK RHLTQRLENL DGKMDEQVEV SKAIRNEVND
VKDDLSQIGF DVESIQKMVA GLEGKIELLE NKQDVANTGI WYLCQVAGGL KDGINTRFFQ
ETSEKLKLSH SAQPENKPVK GLEFFSESTM EQKVADSKPI AVTVDAEKPE KTAAVMGTTV
HRSIRFSYRK AGLAL SEQ ID NO: 17
ATGTGCTCGGTAGCGAGGCTGGCGTTTGTGCTTGCACTGGCCATAGCCGCCTCGTCAATTGAGGTTGCGG
AGAGCAGAGATTTTAATATCTTTGCTCAGGGCAGCTTGCCTGATGCAACCAAGGGATCGTCTGGTCTAGC
TGCAACCAGTGGAAAGTTGTGTCAGTTATGCGAGCAGTACTCATCCGAGGCGCTCCTCTATCTCACACAA
AACGAGACCCAGACTGAGATTCTTAGCATTCTACACCATGAATGTGCCAGCCTTGCCCCTCTCAAACAGC
AGTGCATCACGCTGGTTGACTACTACGTACCCCTTTTCTTCTTGGAGGTCTCCATGGTTACCCCTGAGAA
GTTCTGCGAGTCGATGCATCTCTGCAAGAAGGGGATGAAGATTAGCCTACCCACCCGGGAGGGTACTTGT
GGTTTGTGCCACCATGTTGTTGTTGAAATTCTTATCATGCTTAAAGACCCCAACATGCAGCTGGAAGTAA
TCGACCTACTCACCAAAACATGCAGCAAGGCGCAGAACTATGAACAGTAG SEQ ID NO: 18
MCSVARLAFV LALAIAASSI EVAESRDFNI FAQGSLPDAT KGSSGLAATS GKLCQLCEQY
SSEALLYLTQ NETQTEILSI LHHECASLAP LKQQCITLVD YYVPLFFLEV SMVTPEKFCE
SMHLCKKGMK ISLPTREGTC GLCHHVVVEI LIMLKDPNMQ LEVIDLLTKT CSKAQNYEQ SEQ ID NO: 19
GGACACTGACATGGACTGAAGGAGTAGAAAATCCATCCATTCCCCTCGCCAAGCCGCCACGGCCTGACTT
TCCCTCCCGCACACCCGCGACCATACAGGCAAGTCAGGCATACACCAACAACGCTCGTCGTGCACCTCGC
GCCTCAGGTCACCCCACCCAAATTCCTCTTGATACGCCGAATTTCTTTTGCTAATTCTGCTACCTCCTGTC
GCTAAGCCACCATATTCAGTCTAACCCCTGCTCTGAGCTCACCTGATTGGCGGCTCCGTTCGGCCTCTGG
GCCTGGGTGTACCGACTACCGAGGGCTCTTTCGAAATGTCAATTGGGTCGAGTTTGGTGGGCTACGTGAA
GCATGGATGAATTTCCCGGCTGGAAGCGGGAGGCGGCAGCAGCATCCGGGGCCGGAGCACCTGTCGCCGA
TGACGCCGCTCCCGCTGGCGCGGTAGGGGTCGGTCTACTCGCTCACGTTCGACGAGTTCCAGAGCTCGCT
CGGTGGGGCCACCAAGGACTTCGGATCCATGAACATGGACGAGCTCCTCCGCAACATCTGGTCGGCGGAG
GAGACACACAGCGTCACAGCTGCGGACCATGCCGCGGGCGCCGTACGTCCAGTGCCAGGGCTCGCTCA
CCCTCCCCTGCACGCTCAGCCAGAAGACCGTCGACGAGGTCCGTCTAGCGTGACCTCGTGTGCAACGGTGGAGG
ACCCTCCGACGAGGCTGTGGCGCCGCCCCACCGGCCCAACGCAGCCGACGCTCGGGGAGATCATGCTGG
AGGAGTTCCTCGTCCGCGCCGGCGTGGTGAGGGAGGACATGATGGCGGCGGCGCCCGTACCACCAGCGCC
GGGTTGCCCACCACCTCATCTGCAACCGCCAATGCTGTTTCCACATGGCAATGTGTTTGCTCCCTTAGTG
CCTCCGCTCCAATTCGGGAATGGGTTTGTGTCGGGGCTCTCAGTCAGCAGCAGGGAGGTGTTCTTGAGG
CCCCGGCGGTATCGCCGCGGCCGGTGACGGCAAGCGGGTTCGGGAAGATGAAGGAGACGACTTGTCGCA
TCTGTCGCCATCACCGGTGTCGTACGTTTTTTTGTGCTGGTTTGAGGGGAAGGAAGCCACCAGCTGTGGA
GAAGGTGGTTGAGAGGAGGCAACGCC SEQ ID No: 20
mdfpggsgrq qqlppmtplp larqgsvysl tfdefqstlg gvgkdfgsmn mdellrsiwt
aeeshavgaa ttttattasv aaaehaavga ppvqrqgslt lprtlsqktv devwrdmmcf
ggggastapa aaeppppahr qqtlgeitle eflvragvvr edmsvppvpp aptptaaavp
pppppqqqtp mlfgqsnvfp pmvpplslgn glvsgavghg gggaaslvsp vrpvssngfg
kmeggdlssl spspvpyvfk gglrgrkapg iekvv errqr rmiknresaa rsrqrkqaym
meleaevakl kelndelqkk qdemleqqkn evlermsrqv gptakriclr rtltgpw
```

SEQ ID NO: 21
```
atg gattttccgg gagggagcgg
gaggcagcag cagctgccgc cgatgacgcc gctgccgttg gcgaggcagg ggtcggtgta
ctcgctcacg ttcgacgagt tccagagcac gctgggcggg gtcgggaagg acttcgggtc
gatgaacatg gacgagctcc tccgcagcat ctggacggcc gaggagtcgc acgccgtcgg
cgccgccacg acgacgacgg cgacgacggc gtccgtgacg gcggcggagc acgcggcggt
gggggcgccg cccgttcaga ggcagggggtc gctgaccctc ccccgcacgc tcagccagaa
gaccgtcgac gaggtctggc gcgacatgat gtgcttcggt ggcggcggcg cctccaccgc
gccggccgcc gcggagcccc cgccgccggc gcaccgcag cagacgctcg gggagatcac
gctggaggag ttcctcgtgc gggccggcgt ggtgagggag gacatgtcgg tcccgcccgt
cccgccggcc ccgactccta cggcggctgc tgtacctccc ccgccgccgc cgcagcagca
gacgccgatg ttgttcggtc agagcaatgt gttccctccg atggtgcctc cgctctcgct
gggaaatggg ctggtctcgg gagctgtcgg acacggcggt ggtggtgccg cgtcgttggt
ttcgccggtg aggccggtct cgtccaatgg cttcggcaag atggaaggcg gggacctgtc
gtcgctgtcg ccatcgccgg tgccgtacgt tttcaaaggt gggctgaggg gaaggaaggc
accgggcatc gagaaggttg tcgagagaag acagcggcgg atgatcaaga acagggagtc
tgccgcgagg tcgcgccaga ggaaacaggc atatatgatg gaattggaag ctgaggtagc
aaaacttaag gagctgaacg atgaactcca gaaaaagcag gatgaaatgt tggagcagca
aaagaatgag gttctagaga gaatgagccg acaagttgga ccgacagcaa agagaatttg
ccttcggagg actctgacgg gtccatggtg a
```

SEQ ID NO: 22
```
ATGAATTTCCCGGCTGGAAGCGGGAGGCGGCAGCAGCATCCGGGGCCGGAGCACCTGTCGCCGATGACGC
CGCTCCCGCTGGCGCGGCAGGGGTCGGTCTACTCGCTCACGTTCGACGAGTTCCAGAGCTCGCTCGGTGG
GGCCACCAAGGACTTCGGATCCATGAACATGGACGAGCTCCTCCGCAACATCTGGTCGGCGGAGGAGACA
CACAGCGTCACAGCTGCGGACCATGCCGCGGGCGCCGTCTACGTCCAGTGCCAGGGCTCGCTCACCCTCC
CCTGCACGCTCAGCCAGAAGACCGTCGACGAGGTCTGGCGTGACCTCGTGTGCAACGGTGGAGGACCCTC
CGACGAGGCTGTGGCGGCCGCCCCACCGGCCCAACGGCAGCCGACGCTCGGGGAGATCATGCTGGAGGAG
TTCCTCGTCCGCGCCGGCGTGGTGAGGGAGGACATGATGGCGGCGGCGCCCGTACCACCAGCGCCGGGTT
GCCCACCACCTCATCTGCAACCGCCAATGCTGTTTCCACATGGCAATGTGTTTGCTCCCTTAGTGCCTCC
GCTCCAATTCGGGAATGGGTTTGTGTCGGGGGCTCTCAGTCAGCAGCAGGGAGGTGTTCTTGAGGCCCCG
GCGGTATCGCCGCGGCCGGTGACGGCAAGCGGGTTCGGGAAGATGGAAGGAGACGACTTGTCGCATCTGT
CGCCATCACCGGTGTCGTACGTTTTTTTTGTGCTGGTTTGAGGGGAAGGAAGCCACCAGCTGTGGAGAAGG
TGGTTGA
```

SEQ ID NO: 23
```
MNFPAGSGRR QQHPGPEHLS PMTPLPLARQ GSVYSLTFDE FQSSLGGATK DFGSMNMDEL
LRNIWSAEET HSVTAADHAA RAPYVQCQGS LTLPCTLSQK TVDEVWRDLV CNGGGPSDEA
VAAAPPAQRQ PTLGEIMLEE FLVRAGVVRE DMMAAAPVPP APGCPPPHLQ PPMLFPHGNV
FAPLVPPLQF GNGFVSGALS QQQGGVLEAP AVSPRPVTAS GFGKMEGDDL SHLSPSPVSY
VFLCWFEGKE ATSCGEGG
```

SEQ ID NO: 24
```
ATGAATTTCCCGGCTGGAAGCGGGAGGCGGCAGCAGCATCCGGGGCCGGAGCACCTGTCGCCGATGACGC
CGCTCCCGCTGGCGCGGCAGGGGTCGGTCTACTCGCTCACGTTCGACGAGTTCCAGAGCTCGCTCGGTGG
GGCCACCAAGGACTTCGGATCTATGAACATGGACGAGCTCCTCCGCAACATCTGGTCGGCGGAGGAGACA
CACAGCGTCACAGCTGCGGACCATGCCGCGGGCGCCGTCTACGTCCAGTGCCAGGGCTCGCTCACCCTCC
CCTGCACGCTCAGCCAGAAGACCGTCGACGAGGTCTGGCGTGACCTCGTGTGCAACGGTGGAGGACCCTC
CGACGAGGCTGTGGCGGCCGCCCCACCGGCCCAACGGCAGCCGACGCTCGGGGAGATCATGCTGGAGGAG
TTCCTCGTCCGCGCCGGCGTGGTGAGGGAGGACATGATGGCGGCGGCGCCCGTACCACCAGCGCCGGGTT
GCCCACCACCTCATCTGCAACCGCCAATGCTGTTTCCACATGGCAATGTGTTTGCTCCCTTAGTGCCTCC
GCTCCAATTCGGGAATGGGTTTGTGTCGGGGGCTCTCAGTCAGCAGCAGGGAGGTGTTCTTGAGGCCCCG
GCGGTATCGCCGCGGCCGGTGACGGCAAGCGGGTTCGGGAAGATGGAAGGAGACGACTTGTCGCATCTGT
CGCCATCACCGGTGTCGTACGTTTTTTTTGTGCTGGTTTGAGGGGAAGGAAGCCACCAGCTGTGGACAAGG
TGGTGAGAGAAGACAGAGGAGGATGATCAAGAACAGGGAGTCTGCCGCGAGGTCGAGGCAGAGGAAACAG
GCATATATGATGGAATTGGAAGCTGAGGTAGCAAAGCTCAAGGAGCTGAACGACGAGCTCCAGAAGAAGC
AGGACGAGATGCTGGAGCAGCAGAAGAACGAGGTGCTGGAGAGGATGTCCAGGCAGGTGGGCCCAACCGC
CAAGAGGATTTGCCTGAGGAGGACCCTGACCGGCCCATGGTGA
```

SEQ ID NO: 25
```
MNFPAGSGRR QQHPGPEHLS PMTPLPLARQ GSVYSLTFDE FQSSLGGATK DFGSMNMDEL
LRNIWSAEET HSVTAADHAA RAPYVQCQGS LTLPCTLSQK TVDEVWRDLV CNGGGPSDEA
VAAAPPAQRQ PTLGEIMLEE FLVRAGVVRE DMMAAAPVPP APGCPPPHLQ PPMLFPHGNV
FAPLVPPLQF GNGFVSGALS QQQGGVLEAP AVSPRPVTAS GFGKMEGDDL SHLSPSPVSY
VFLCWFEGKE ATSCGQGGER RQRRMIKNRE SAARSRQRKQ AYMMELEAEV AKLKELNDEL
QKKQDEMLEQ QKNEVLERMS RQVGPTAKRI CLRRTLTGPW
```

SEQ ID NO: 26
```
ATGATGTTCTCCTCCTCCCTCTCTGTGGTGGAGTTTTACTTCCTGCACAGATTCCCCCTGCCTTTTGCTG
GCTACCTCATCTTCATTTCCATATTGGCTGGATTCTGGGGCCAGTGTTTGGTTAGGAAGATCGTGCATGT
GCTCAAGAGAGCATCGCTTATTGTCTTCATCCTCTCCTCTGTTATCTTCGTCAGTGCTCTTACGATGGGT
GTCGTTGGAACCCAGAAGAGCATTTCGATGATCAACAATCACGAATATATGGGGTTCCTCAACTTCTGCG
AGTAA
```

SEQ ID NO: 27
```
MMFSSSLSVV EFYFLHRFPL PFAGYLIFIS ILAGFWGQCL VRKIVHVLKR ASLIVFILSS
VIFVSALTMG VVGTQKSISM INNHEYMGFL NFCE
```

SEQ ID NO: 28
```
ATGGCGTCTGCAGTGACCAGCAGCGACAAGGAGCAGGCCGTCCCTACCATCGACGCTGACGAAGCGCACG
CGCTGCTGAGCTCCGGCCATGGCTACGTGGATGTCAGGATGCGGGGGGACTTCCACAAGGCGCATGCGCC
```

```
CGGTGCTCGGAACGTTCCCTACTACCTGTCCGTCACGCCGCAAGGGAAGGAGAAGAACCCACACTTTGTA
GAGGAAGTGGCTGCCTTCTGTGGGAAGGATGATGTCTTCATTGTGGGTTGCAACACGGGGAACAGATCCA
GGTTCGCGACGGCAGACCTTCTGAACGCGGGGTTCAAGAACGTGAGGAACCTGCAAGGTGGTTACCGCTC
CTTTCAGCAGCGAGCTAACAGCAGTA

SEQ ID NO: 29
MASAVTSSDK EQAVPTIDAD EAHALLSSGH GYVDVRMRGD FHKAHAPGAR NVPYYLSVTP
QGKEKNPHFV EEVAAFCGKD DVFIVGCNTG NRSRFATADL LNAGFKNVRN LQGGYRSFQQ
RAQQQ

SEQ ID NO: 30
ATGGAGGCGAAGAAGAAGCCGTCGGCCCCCGCCGCCGTCGGAGCCGCGCCGCCGCCGCCGGGTAACGGGT
ACTTCAGCACCGTCTTCTCCGCGCCGACTGCGGGAAGCGCAAGTGACGCAAAGCATGCGGACTTGTACAC
GATGCTGAACAAGCAGAGCTCCAGAGGGCAGAATGGCAGAGATGGCAAATCCCACAGCCGCCCTTACTTAC
AAGGATGGCAAACATGCTCATCCAAATGAGCCATCAGAATCCTTACTTTGGCTCATCCGTGCATTACG
GTGGTCGGGAGTTCTACAGCAGCGTTTTACGGAAGCAACCAGCCAATGAACCCCATACGGATTACAAGGG
GGACAACCCGGATGGCTCTGCTACCAGAGGTGATTGGTGGCAAGGTTCACTTTATTACTGA

SEQ ID NO: 31
MEAKKKPSAP AAVGAAPPPP GNGYFSTVFS APTAGSASDA KHADLYTMLN KQSSRGQNGR
DGKSHSRPTY KDGKHAHPNE PSESPYFGSS VHYGGREFYS SVLRKQPANE PHTDYKGDNP
DGSATRGDWW QGSLYY

SEQ ID NO: 32
ATGGACCGGAACCTGAGCGGGTTTCTGATCGGGTGCCTGGGCGCCGCCGTGACGCTGCTGGCGTACCAGC
AGACGGTGGTGACCAGCACGCAGAGCGTCGCGGCGGGCTTCGTCGTCATCCTCTTCGCCCTCTTCGTCAA
GGAAGGATTCATTTCCCTCTGA

SEQ ID NO: 33
MDRNLSGFLI GCLGAAVTLL AYQQTVVTST QSVAAGFVVI LFALFVKEGF ISL

SEQ ID NO: 34
ATGGCATGCGTCAGCACCTTCCAGAGCTGCCCCATTGCCAGAAGAGCAAAGATCAACACCAGGTCCAGGG
GCAGCAGTAGCGTGGCGAAGGGGTCACCACCACCAGCCTTCCAGTTCCAGTGCAGGGCGTCGACTTT
CGCGGCGGACACCAGCCTCCGGCTCGAGCTGGACGAGAACCCCGAGGCGATCATCTCGGGGGCGTGGCCC
GGGAACTGCTCCCTCCTCAGCTACGACGACCTCCGCGCCTACCTCGAGTCGCAGGAGACGGCGGCCCAGG
CAGACGATCAGCGCGGCGTGGCGCTCCTGAGCGAGACCATGTCCACACCCGTGCTGGTGGCCACAGCAGA
CCAGACCCTGGAGGACGTCGAGTGCCACTTCGAGGCCGTGTCGGGGCTTCCGGTCGTCGACAGCGGCCTC
AGATGCGTCGGGGTGATCGTCAAGAACGACCGGGCAAGAGCCTCTCATGGGTCCAAGACGAAGATATCGG
AAGTGATGACATCTCCAGCTATCACACTATCGTCTGACAAAACCGTGATGGATGCTGCTGTTCTCATGCT
CAAGAAGAAGATCCACAGATTACCAGTTGTAAACCAGGACGAAAAAGTAATAGGTATAGTTACCCGCGCT
GATGTTCTTCGCGTGTTGGAAGGCATGTTGAAGATTTAG

SEQ ID NO: 35
MACVSTFQSC PIARRAKINT RSRGSSSSVA KGSPPPAFQF QCRASTFAAD TSLRLELDEN
PEAIISGAWP GNCSLLSYDD LRAYLESQET AAQADDQRGV ALLSETMSTP VLVATADQTL
EDVECHFEAV SGLPVVDSGL RCVGVIVKND RARASHGSKT KISEVMTSPA ITLSSDKTVM
DAAVLMLKKK IHRLPVVNQD EKVIGIVTRA DVLRVLEGML KI

SEQ ID NO: 36
ATGGGCGACCTCTCTGTCGGCCACAGCCGCCGCTGGTGCGGCCGTTTCGCGGCCGTTCCTTTGCCTGTCG
CGGCCTTCTGCAAGCCAGATGAACTCCCGATGGATCCACTGCCGAACTTGCCGCCGACGAGGTCGCTGCA
GTGCTTCGAGGACGAACAGGTGTACAGCTGCTGCGAGGGCGCGTACAGGCTAAACCCATCGGGAATCATC
GCCGTTCCCGTCGGCGCGGTGGACTACTACTGCGGCGGCGCGTGCGTGGTGGAGACGGAGGACGTGCTCA
ACTGCGTGGCCAGCGCCCTGGACGGCTTCGCCTTCTACAACGGGGCCTCCGTGGAGGACGTGCGACTACGC
ACTCAGGCGGGGCTGCAGCCACACCGCCAGAAGAGGCGACTTCAACGATTTGGAGCCGCATCTGGGCGAC
TACCCTGACATCTATGGCGACGATGATGAGCACAGCTTTGGCAGCAAGGTTGTTGCAGCTCCTCTGAGGT
TGCTCGCGTTTCTTGGCGGTGCGGGGCTGTTCTTCCTGGGCCCTTGA

SEQ ID NO: 37
MGDLSVGHSR RWCGRFAAVL CLCAAFCKPD ELPMDPLPNL PPTRSLQCFE DEQVYSCCEG
AYRLNPSGII AVPVGAVDYY CGGACVVETE DVLNCVASAL DGFAFYNGAS VEDVRYALRR
GCSHTARRGD FNDLEPHLGD YPDIYGDDDE HSFGSKVVAA PLRLLAFLGG AGLFFLGP

SEQ ID NO: 38
ATGGATTCGGAGGCGGTGCAGCACGGCCTTCTCCCTCTGTCTGCCTGTCCTCCTACCGCCAACAGCTGCG
CGCATTACAGCCGTGGGTGCAGCGTCGTGGCGCCCTGCTGCGGCCAGGCCTTCGGCTGCCGCCATTGCCA
CAACGACGCCAAGAACTCGCTGGAGGTCGACCCGCGCGACCGGCACGAGATCCCCCGCCACGAAATAAAG
AAGGTGATCTGTTCTCTCTGCTCCAAGGAACAGGACGTGCAACAGAACTGCTCCAGCTGTGGGGCCTGCA
TGGGCAAGTACTTCTGTAAAGTATGCAAGTTCTTCGATGATGATGCCTCAAAGGGCCAGTACCACTGTGA
CGGATGTGGAATATGTAGAACCGGCGGCGTGGAGAACTTTTTTCCACTGTGATAAATGTGGGTGTTGCTAC
AGCAATGTCTTGAAGGATTCCCACCACTGCGTCGAAAAGACAATGCATCACAACTGCCCCGTCTGCTTTG
AGTATCTGTTCGACTCCACGAAGGACATCAGCGTGCTGCAATGTGGGCATACCATCCATTTGGAGTGCAT
GACGAGATGAGAGCACACCATCACTTCTCATGCCCAGTGTGCTCGAGGTCCGCCTGCGACATGTCGGCC
ACATGGCGGAAGCTCGACGAGGAGGTCGCGGCCACGCCGATGCCTGACATCTACCAGAAGCACATGGTGT
GGATCCTGTGCAACGACTGCAGCGCGACCTCGAGCGTGCGGTTCCACGTGCTGGGGCACAAGTGCCCCGC
GTGCAGCTCGTACAACACCCGGGAGACGAGGGCTGCTGCCCCAGGATCTGA

SEQ ID NO: 39
MDSEAVQHGL LPLSACPPTA NSCAHYSRGC SVVAPCCGQA FGCRHCHNDA KNSLEVDPRD
RHEIPRHEIK KVICSLCSKE QDVQQNCSSC GACMGKYFCK VCKFFDDDAS KGQYHCDGCG
```

ICRTGGVENF FHCDKCGCCY SNVLKDSHHC VERAMHHNCP VCFEYLFDST KDISVLQCGH
TIHLECMNEM RAHHHFSCPV CSRSACDMSA TWRKLDEEVA ATPMPDIYQK HMVWILCNDC
SATSSVRFHV LGHKCPACSS YNTRETRAAC PRI

We claim:

1. A method for increasing nitrogen utilization efficiency in a plant comprising:
    (a) transforming a plant cell with an expression vector comprising an isolated nucleic acid molecule that encodes the amino acid sequence set forth in SEQ ID NO: 31;
    (b) expressing said nucleic acid molecule in said plant cell under control of a heterologous promoter;
    (c) generating from said plant cell a plurality of transformed plants in which said nucleic acid molecule is expressed; and
    (d) selecting from the plurality of said transformed plants a plant having increased nitrogen utilization efficiency as compared to a control plant grown under the same conditions.

2. The method according to claim 1, said expression vector further comprising a 5' DNA promoter sequence and a 3' terminator sequence, wherein the nucleotide sequence, the DNA promoter sequence, and the terminator sequence are operatively coupled to permit transcription of the nucleotide sequence.

3. The method according to claim 2, wherein the promoter sequence is selected from the group consisting of constitutive plant promoters and tissue specific promoters.

4. The method according to claim 1, further comprising the step of growing said plant having increased nitrogen utilization efficiency to produce transgenic plant seed.

5. A method of expressing a nucleic acid molecule in a plant having improved nitrogen utilization, said method comprising the steps of providing a transgenic plant or plant seed transformed according to the method of claim 4, and growing the transgenic plant or a plant grown from the transgenic plant seed under conditions effective to express the nucleic acid molecule in said transgenic plant or said plant grown from the transgenic plant seed, thereby resulting in expression of the nucleic acid molecule in the plant having improved nitrogen utilization.

6. The method according to claim 5, wherein expression of the nucleic acid molecule is effective in increasing nitrogen uptake of said transgenic plant or said plant grown from the transgenic plant seed as compared to a control plant grown under the same conditions.

7. The method according to claim 5, wherein expression of the nucleic acid molecule is effective in increasing efficiency of nitrogen utilization of said transgenic plant or said plant grown from the transgenic plant seed as compared to a control plant grown under the same conditions.

8. The method according to claim 5, wherein the plant is selected from the group consisting of rice, corn, soybean, canola, wheat, alfalfa, barley, rye, cotton, sunflower, peanut, sweet potato, bean, pea, potato, oilseed rape, sorghum, grasses, and sugarcane.

9. The method according to claim 5, wherein expression of the nucleic acid molecule is effective in improving the stress tolerance of said transgenic plant or said plant grown from the transgenic plant seed as compared to a control plant grown under the same conditions.

10. A method for increasing nitrogen utilization efficiency in a plant of *Zea mays* comprising:
    (a) transforming a *Zea mays* plant cell with an expression vector comprising an isolated nucleic acid molecule that encodes the amino acid sequence set forth in SEQ ID NO: 31;
    (b) expressing said nucleic acid molecule in said plant cell under control of a heterologous promoter;
    (c) generating from said plant cell a plurality of transformed plants in which said nucleic acid molecule is expressed; and
    (d) selecting from the plurality of said transformed plants a plant having increased nitrogen utilization efficiency as compared to a control plant grown under the same conditions.

11. The method according to claim 10, said expression vector further comprising a 5' DNA promoter sequence and a 3' terminator sequence, wherein the nucleotide sequence, the DNA promoter sequence, and the terminator sequence are operatively coupled to permit transcription of the nucleotide sequence.

12. The method according to claim 11, wherein the promoter sequence is selected from the group consisting of constitutive plant promoters and tissue specific promoters.

13. A method of expressing a nucleic acid molecule in a *Zea mays* plant having improved nitrogen utilization, said method comprising the steps of providing a transgenic *Zea mays* plant or plant seed transformed according to the method of claim 4, and growing the transgenic plant or a plant grown from the transgenic plant seed under conditions effective to express the nucleic acid molecule in said transgenic plant or said plant grown from the transgenic plant seed, thereby resulting in expression of the nucleic acid molecule in the plant having improved nitrogen utilization.

14. The method according to claim 13, wherein expression of the nucleic acid molecule is effective in increasing nitrogen uptake of said transgenic plant or said plant grown from the transgenic plant seed as compared to a control plant grown under the same conditions.

15. The method according to claim 13, wherein expression of the nucleic acid molecule is effective in increasing efficiency of nitrogen utilization of said transgenic plant or said plant grown from the transgenic plant seed as compared to a control plant grown under the same conditions.

16. The method according to claim 13, wherein expression of the nucleic acid molecule is effective in improving the stress tolerance of said transgenic plant or said plant grown from the transgenic plant seed as compared to a control plant grown under the same conditions.

* * * * *

SEQUENCE LISTING

<160> NUMBER OF SEQ ID NOS: 39

<210> SEQ ID NO 1
<211> LENGTH: 380
<212> TYPE: DNA
<213> ORGANISM: Zea mays

<400> SEQUENCE: 1

```
tcgactggag cacgaggaca ctgacatgga ctgaaggagt agaaaatcac ctagctagaa      60
aggagagcac cgagcgctgc accactactg ctgatatgag cacctgaacc ttctgggcaa     120
ccacatcgtc cctgcccctg atcatccgca gcagccatgg cgcagcagca ggagaagaag     180
cagcagcaga gggggaagct gcagagggtg ctaagggagc agaaggctcg gctctacatc     240
atccgccgat gcgcgtcatg ctcctctgct ggagtgactg atccatctca agcatgcatg     300
ataaacctgt gctctttttt tttccttctg ttttttcccc tcttttccc atcctttca      360
ccttgccact tggtgggcg                                                  380
```

<210> SEQ ID NO 2
<211> LENGTH: 125
<212> TYPE: DNA
<213> ORGANISM: Zea mays

<400> SEQUENCE: 2

```
atggcgcagc agcaggagaa gaagcagcag cagagggga agctgcagag ggtgctaagg       60
gagcagaagg ctcggctcta catcatccgc cgatgcgcgt catgctcctc tgctggagtg     120
actga                                                                 125
```

<210> SEQ ID NO 3
<211> LENGTH: 41
<212> TYPE: PRT
<213> ORGANISM: Zea mays

<400> SEQUENCE: 3

```
Met Ala Gln Gln Gln Glu Lys Lys Gln Gln Gln Arg Gly Lys Leu Gln
1               5                   10                  15
Arg Val Leu Arg Glu Gln Lys Ala Arg Leu Tyr Ile Ile Arg Arg Cys
            20                  25                  30
Val Val Met Leu Leu Cys Trp Ser Asp
        35                  40
```

<210> SEQ ID NO 4
<211> LENGTH: 801
<212> TYPE: DNA
<213> ORGANISM: Zea mays

<400> SEQUENCE: 4

```
atgtgcattg ctgcatggat tggcaggct caccctgtgc accaactcct cctgcttctc        60
aacagagatg agttccacag caggcctaca aaagcagtag gatggtgggg tgaaggctca      120
aagaagatcc ttggtggcag ggatgtgctt ggtggaggaa catggatggg gtgcaccaag      180
gatgaaggc ttgccttcct gaccaatgtg cttgaaccag atgccatgcc cggtgcacgg       240
actaggggag atctgcctct caaattcctg cagagcaaca agagcccact cgaagttgca      300
```

```
actgaagtgg cagaagaagc tgatgaatac aatggcttca acctcatact agctgatcta    360
acaacaaata tcatggttta tgtgtcaaac cggcctaagg gtcagcctgc aacaattcaa    420
ctcgtgtcac caggactcca tgtgctgtcc aatgcaaggc tagatagccc ttggcagaag    480
gcaattctcc tcggtaaaaa cttcagggag cttcttaggg agcatggtgc tgatgaggtt    540
gaagtgaagg atatagttga gaggctaatg actgacacca caaaggctga caaagataga    600
ctgccaaaca ctggttgtga tcccaactgg gagcatggtc tgagctccat cttcattgag    660
gtgcaaactg accaagggcc ctatgggaca cggagcacag ccgttttatc agtgaactat    720
gatggcgaag ctagcttgta cgagaagtat cttgagagtg gtatatggaa ggatcacaca    780
gtgagttacc agatagagta g                                              801
```

```
<210> SEQ ID NO 5
<211> LENGTH: 266
<212> TYPE: PRT
<213> ORGANISM: Zea mays

<400> SEQUENCE: 5
```

| | | | | | | | | | | | | | | |
|---|---|---|---|---|---|---|---|---|---|---|---|---|---|---|
Met Cys Ile Ala Ala Trp Ile Trp Gln Ala His Pro Val His Gln Leu
  1               5                  10                  15

Leu Leu Leu Leu Asn Arg Asp Glu Phe His Ser Arg Pro Thr Lys Ala
             20                  25                  30

Val Gly Trp Trp Gly Glu Gly Ser Lys Lys Ile Leu Gly Gly Arg Asp
         35                  40                  45

Val Leu Gly Gly Gly Thr Trp Met Gly Cys Thr Lys Asp Gly Arg Leu
     50                  55                  60

Ala Phe Leu Thr Asn Val Leu Glu Pro Asp Ala Met Pro Gly Ala Arg
 65                  70                  75                  80

Thr Arg Gly Asp Leu Pro Leu Lys Phe Leu Gln Ser Asn Lys Ser Pro
                 85                  90                  95

Leu Glu Val Ala Thr Glu Val Ala Glu Glu Ala Asp Glu Tyr Asn Gly
            100                 105                 110

Phe Asn Leu Ile Leu Ala Asp Leu Thr Thr Asn Ile Met Val Tyr Val
        115                 120                 125

Ser Asn Arg Pro Lys Gly Gln Pro Ala Thr Ile Gln Leu Val Ser Pro
    130                 135                 140

Gly Leu His Val Leu Ser Asn Ala Arg Leu Asp Ser Pro Trp Gln Lys
145                 150                 155                 160

Ala Ile Leu Leu Gly Lys Asn Phe Arg Glu Leu Leu Arg Glu His Gly
                165                 170                 175

Ala Asp Glu Val Glu Val Lys Asp Ile Val Glu Arg Leu Met Thr Asp
            180                 185                 190

Thr Thr Lys Ala Asp Lys Asp Arg Leu Pro Asn Thr Gly Cys Asp Pro
        195                 200                 205

Asn Trp Glu His Gly Leu Ser Ser Ile Phe Ile Glu Val Gln Thr Asp
    210                 215                 220

Gln Gly Pro Tyr Gly Thr Arg Ser Thr Ala Val Leu Ser Val Asn Tyr
225                 230                 235                 240

Asp Gly Glu Ala Ser Leu Tyr Glu Lys Tyr Leu Glu Ser Gly Ile Trp
                245                 250                 255

Lys Asp His Thr Val Ser Tyr Gln Ile Glu
            260                 265

<210> SEQ ID NO 6
<211> LENGTH: 687
<212> TYPE: DNA
<213> ORGANISM: Zea mays

<400> SEQUENCE: 6

```
attcccgtct tacctagcgc tagggttagt acgcgtccac ggcgacgacc tctgcgcgga     60
gtgtgctccg attggctggc ctcctcgatc ctccttcccg cgaacgcacg cgcgcgcgag    120
ggagaggttg agacttgaga gatagacgaa agacgaaaca agggaaggag acgccgtgct    180
cgcctattgg ccgccgcctc cgctccttcg cgcccaatgg cttctgcagc atatcaatat    240
catgcagcat agcagtactc agacccttac tacgcaggcg ttgttgctcc ctatggaagt    300
caagatgtgt gtccgaggag cctgtctatg tgaacgccaa gcagtaccgc ggcattctaa    360
gacggcggca gtcacgtgcc aaggccgagc ttgagagaaa gcgctggtca agcaagaaa    420
gccgtatctt cacgagtccc cgtcatcagc acgcgatgac gaggagggcg agagggaacg    480
gtggacgctt cctaaacacg aagaagagtg accgtgtccc tcctgatgac ttgatacagc    540
tacgacgaca caacgaggct tgaagaggta gcggtctggc tggcatccta gagcagcggt    600
ttctgtccac aggcacgtgc atctgagacc ggatccgtag ctccactcca cagcatatgc    660
gcagcccatc catctcgtgc acacttg                                        687
```

<210> SEQ ID NO 7
<211> LENGTH: 153
<212> TYPE: DNA
<213> ORGANISM: Zea mays

<400> SEQUENCE: 7

```
atgcagcata gcagtactca gacccttact acgcaggcgt tgttgctccc tatggaagtc     60
aagatgtgtg tccgaggagc ctgtctatgt gaacgccaag cagtaccgcg gcattctaag    120
acggcggcag tcacgtgcca aggccgagct tga                                 153
```

<210> SEQ ID NO 8
<211> LENGTH: 50
<212> TYPE: PRT
<213> ORGANISM: Zea mays

<400> SEQUENCE: 8

```
Met Gln His Ser Ser Thr Gln Thr Leu Thr Thr Gln Ala Leu Leu Leu
1               5                   10                  15
Pro Met Glu Val Lys Met Cys Val Arg Gly Ala Cys Leu Cys Glu Arg
            20                  25                  30
Gln Ala Val Pro Arg His Ser Lys Thr Ala Ala Val Thr Cys Gln Gly
        35                  40                  45
Arg Ala
    50
```

<210> SEQ ID NO 9
<211> LENGTH: 429
<212> TYPE: DNA
<213> ORGANISM: Zea mays

<400> SEQUENCE: 9

```
ttgagagata gacgaaagac gaaacaaggg aaggagacgc cgtgctcgcc tattggccgc     60
cgcctccgct ccttcgcgcc caatggcttc tgcagcatat caatatcatg cagcatagca    120
gtactcagac ccttactacg caggcgttgt tgctccctat ggaagtcaag atgtgtgtcc    180
```

```
gaggagcctg tctatgtgaa cgccaagcag taccgcggca ttctaagacg gcggcagtca    240
cgtgccaagg ccgagcttga gagaaagcgc tggtcaaagc aagaaagccg tatcttcacg    300
agtccccgtc atcagcacgc gatgacgagg agggcgagag ggaacggtgg acgcttccta    360
aacacgaaga agagtgaccg tgtccctcct gatgacttga tacagctacg acgacacaac    420
gaggcttga                                                            429
```

<210> SEQ ID NO 10
<211> LENGTH: 142
<212> TYPE: PRT
<213> ORGANISM: Zea mays

<400> SEQUENCE: 10

```
Leu Arg Asp Arg Arg Lys Thr Lys Gln Gly Lys Glu Thr Pro Cys Ser
1               5                   10                  15

Pro Ile Gly Arg Arg Leu Arg Ser Phe Ala Pro Asn Gly Phe Cys Ser
            20                  25                  30

Ile Ser Ile Ser Cys Ser Ile Ala Val Leu Arg Pro Leu Leu Arg Arg
        35                  40                  45

Arg Cys Cys Ser Leu Trp Lys Ser Arg Cys Val Ser Glu Glu Pro Val
    50                  55                  60

Tyr Val Asn Ala Lys Gln Tyr Arg Gly Ile Leu Arg Arg Arg Gln Ser
65                  70                  75                  80

Arg Ala Lys Ala Glu Leu Glu Arg Lys Arg Trp Ser Lys Gln Glu Ser
                85                  90                  95

Arg Ile Phe Thr Ser Pro Arg His Gln His Ala Met Thr Arg Arg Ala
            100                 105                 110

Arg Gly Asn Gly Gly Arg Phe Leu Asn Thr Lys Lys Ser Asp Arg Val
        115                 120                 125

Pro Pro Asp Asp Leu Ile Gln Leu Arg Arg His Asn Glu Ala
    130                 135                 140
```

<210> SEQ ID NO 11
<211> LENGTH: 378
<212> TYPE: DNA
<213> ORGANISM: Zea mays

<400> SEQUENCE: 11

```
atgactgctc accagacttg ctgcgatgat gccgttgccg ccggcactgc accggctgcc     60
aggaggaggc gcctcaaatt gacgaggccg tcggcctcgc tcttgatggc gaggaagcta    120
aggaagaagg ctgccggcag caaacgccca agggcggcag cgtcgaggaa gcgcgcgatg    180
gcgatcagga ggaagatgga agcgctgagg ctgctcgtgc cactctgcgg ccgagacaac    240
ggctcggtga ccgtgtgggc ggtcgaacga ctggacgagc tcctcatgca cgccgccggg    300
tacatcctgc gcctccagat gcaggtcaga gtgatgcagc ttatggtcca tgcactaaat    360
gaccggcccg aggattaa                                                  378
```

<210> SEQ ID NO 12
<211> LENGTH: 125
<212> TYPE: PRT
<213> ORGANISM: Zea mays

<400> SEQUENCE: 12

```
Met Thr Ala His Gln Thr Cys Cys Asp Asp Ala Val Ala Ala Gly Thr
1               5                   10                  15

Ala Pro Ala Ala Arg Arg Arg Arg Leu Lys Leu Thr Arg Pro Ser Ala
```

```
        20                  25                  30
Ser Leu Leu Met Ala Arg Lys Leu Arg Lys Ala Ala Gly Ser Lys
         35                  40                  45

Arg Pro Arg Ala Ala Ala Ser Arg Lys Arg Ala Met Ala Ile Arg Arg
 50                  55                  60

Lys Met Glu Ala Leu Arg Leu Leu Val Pro Leu Cys Gly Arg Asp Asn
 65                  70                  75                  80

Gly Ser Val Thr Gly Gly Ala Val Glu Arg Leu Asp Glu Leu Leu Met
                 85                  90                  95

His Ala Ala Gly Tyr Ile Leu Arg Leu Gln Met Gln Val Arg Val Met
                100                 105                 110

Gln Leu Met Val His Ala Leu Asn Asp Arg Pro Glu Asp
                115                 120                 125

<210> SEQ ID NO 13
<211> LENGTH: 792
<212> TYPE: DNA
<213> ORGANISM: Zea mays

<400> SEQUENCE: 13
atgtcggcgg cgctcgcggt gacggacgag gtggccctgc cgatccgggc ggtgggggat      60
ctagcggccg ccgccgaggt ctcgcgggag gaggtcgccg tcatcaccca gtgcgcggcg     120
ctcggtggga agttgccttt tgaagatgca tcagttggtg cggttcttgc agtcattaaa     180
aacgtggaaa gcttgaggga gcaattggtt gctgaaatca ggcgggtgct gaaagctggt     240
ggaagagtat tggtgcagag ccctgcaccc tcatccagtc agaagccgaa cactgatatt     300
gagcgcaagt tactgatggg tggatttgct gaagtgcaat cttctgctgc aagctcgcag     360
gatagcgtgc aatctgttac agttaaggca agaaggcta gctggagcat gggctcttct     420
tttcccctta agaaaacaac aaaagccctt cccaagattc aaattgacga cgactctgat     480
ctgattgatg aagacagtct cttgactgag gaggacctga gaaaccaca acttccagtt     540 gttggggact gtgaggtggg ggcagcaaag aaagcatgca agaactgtac ttgtggcagg     600
gctgaggccg aggagaaggt tgggaagctg gagctcactg cggagcagat caataaccct     660
cagtcagctt gtggcagttg tgggttgggt gatgccttcc gctgtggaac ctgtccctac     720
agaggtcttc caccattcaa gcctggcgag aaggtttcct tgtctggcaa cttccttgct     780
gctgacatat ga                                                        792

<210> SEQ ID NO 14
<211> LENGTH: 263
<212> TYPE: PRT
<213> ORGANISM: Zea mays

<400> SEQUENCE: 14

Met Ser Ala Ala Leu Ala Val Thr Asp Glu Val Ala Leu Pro Ile Arg
 1               5                  10                  15

Ala Val Gly Asp Leu Ala Ala Ala Glu Val Ser Arg Glu Glu Val
                 20                  25                  30

Ala Val Ile Thr Gln Cys Ala Ala Leu Gly Gly Lys Leu Pro Phe Glu
             35                  40                  45

Asp Ala Ser Val Gly Ala Val Leu Ala Val Ile Lys Asn Val Glu Ser
 50                  55                  60

Leu Arg Glu Gln Leu Val Ala Glu Ile Arg Arg Val Leu Lys Ala Gly
 65                  70                  75                  80
```

```
Gly Arg Val Leu Val Gln Ser Pro Ala Pro Ser Ser Gln Lys Pro
             85                  90                  95
Asn Thr Asp Ile Glu Arg Lys Leu Leu Met Gly Gly Phe Ala Glu Val
        100                 105                 110
Gln Ser Ser Ala Ala Ser Ser Gln Asp Ser Val Gln Ser Val Thr Val
        115                 120                 125
Lys Ala Lys Lys Ala Ser Trp Ser Met Gly Ser Ser Phe Pro Leu Lys
130                 135                 140
Lys Thr Thr Lys Ala Leu Pro Lys Ile Gln Ile Asp Asp Asp Ser Asp
145                 150                 155                 160
Leu Ile Asp Glu Asp Ser Leu Leu Thr Glu Glu Asp Leu Lys Lys Pro
                165                 170                 175
Gln Leu Pro Val Val Gly Asp Cys Glu Val Gly Ala Ala Lys Lys Ala
            180                 185                 190
Cys Lys Asn Cys Thr Cys Gly Arg Ala Glu Ala Glu Glu Lys Val Gly
        195                 200                 205
Lys Leu Glu Leu Thr Ala Glu Gln Ile Asn Asn Pro Gln Ser Ala Cys
210                 215                 220
Gly Ser Cys Gly Leu Gly Asp Ala Phe Arg Cys Gly Thr Cys Pro Tyr
225                 230                 235                 240
Arg Gly Leu Pro Pro Phe Lys Pro Gly Glu Lys Val Ser Leu Ser Gly
                245                 250                 255
Asn Phe Leu Ala Ala Asp Ile
            260

<210> SEQ ID NO 15
<211> LENGTH: 948
<212> TYPE: DNA
<213> ORGANISM: Zea mays

<400> SEQUENCE: 15
atggcgatgc agacgggggt cgcgacctcc aaggtcctca tcctcgtcgg tgcagggatg    60
acgggctcga tcctgctgcg gaatggccgc ttatctgatg tgttgggaga actccaggag   120
attatgaagg gtgtaaatca aggaacttct tcgggtccct atgacattgc acttattcaa   180
gctcagattc ggaatttagc gcaagaagtc agagatttga cattgtcaaa gcccattacc   240
atactgaatg caaatctga ctcgggaggc agtttatcat cctacatact gccagcagca   300
gcagttggag caatgggtta ttgctacatg tggtggaagg ggttgtctct ctcagatgtc   360
atgtttgtca aaacacaa catggcaaat gctgttcaga gcatgtcaaa gcagttggag   420
caagtttcat cagcactagc tgcaacaaaa agacatctaa ctcaacggct tgagaatttg   480
gatggcaaaa tggatgaaca agtagaggtc tccaaagcta ttagaaatga ggtcaatgat   540
gttaaagatg acctgtctca aattggattt gatgtcgaat caattcagaa atggttgct   600 ggattggagg gaaagatcga gttacttgag aacaaacagg acgtggctaa tactggtatc   660
tggtatctct gccaagtagc aggcggttta aaagatggaa taaacaccag gttttccag   720 gaaaccagtg agaagctgaa gctctcacat tcagctcaac ctgaaaacaa gccagtgaag   780
gggcttgaat ttttttcgga aagcaccatg aacagaaag tagctgactc caaaccaatt   840
gcggtgacag tcgacgctga aagcctgag aaaaccgctg ctgtaatggg caccacagtg   900
cacaggtcta tcaggttctc atatcggaag gcaggccttg ctttgtga              948

<210> SEQ ID NO 16
<211> LENGTH: 315
```

<212> TYPE: PRT
<213> ORGANISM: Zea mays

<400> SEQUENCE: 16

Met Ala Met Gln Thr Gly Val Ala Thr Ser Lys Val Leu Ile Leu Val
1               5                   10                  15

Gly Ala Gly Met Thr Gly Ser Ile Leu Leu Arg Asn Gly Arg Leu Ser
            20                  25                  30

Asp Val Leu Gly Glu Leu Gln Glu Ile Met Lys Gly Val Asn Gln Gly
        35                  40                  45

Thr Ser Ser Gly Pro Tyr Asp Ile Ala Leu Ile Gln Ala Gln Ile Arg
    50                  55                  60

Asn Leu Ala Gln Glu Val Arg Asp Leu Thr Leu Ser Lys Pro Ile Thr
65                  70                  75                  80

Ile Leu Asn Gly Lys Ser Asp Ser Gly Gly Ser Leu Ser Ser Tyr Ile
                85                  90                  95

Leu Pro Ala Ala Ala Val Gly Ala Met Gly Tyr Cys Tyr Met Trp Trp
            100                 105                 110

Lys Gly Leu Ser Leu Ser Asp Val Met Phe Val Thr Lys His Asn Met
        115                 120                 125

Ala Asn Ala Val Gln Ser Met Ser Lys Gln Leu Glu Gln Val Ser Ser
    130                 135                 140

Ala Leu Ala Ala Thr Lys Arg His Leu Thr Gln Arg Leu Glu Asn Leu
145                 150                 155                 160

Asp Gly Lys Met Asp Glu Gln Val Glu Val Ser Lys Ala Ile Arg Asn
                165                 170                 175

Glu Val Asn Asp Val Lys Asp Asp Leu Ser Gln Ile Gly Phe Asp Val
            180                 185                 190

Glu Ser Ile Gln Lys Met Val Ala Gly Leu Glu Gly Lys Ile Glu Leu
        195                 200                 205

Leu Glu Asn Lys Gln Asp Val Ala Asn Thr Gly Ile Trp Tyr Leu Cys
    210                 215                 220

Gln Val Ala Gly Gly Leu Lys Asp Gly Ile Asn Thr Arg Phe Phe Gln
225                 230                 235                 240

Glu Thr Ser Glu Lys Leu Lys Leu Ser His Ser Ala Gln Pro Glu Asn
                245                 250                 255

Lys Pro Lys Gly Leu Glu Phe Phe Ser Glu Ser Thr Met Glu Gln
            260                 265                 270

Lys Val Ala Asp Ser Lys Pro Ile Ala Val Thr Val Asp Ala Glu Lys
        275                 280                 285

Pro Glu Lys Thr Ala Ala Val Met Gly Thr Thr Val His Arg Ser Ile
    290                 295                 300

Arg Phe Ser Tyr Arg Lys Ala Gly Leu Ala Leu
305                 310                 315

<210> SEQ ID NO 17
<211> LENGTH: 540
<212> TYPE: DNA
<213> ORGANISM: Zea mays

<400> SEQUENCE: 17
atgtgctcgg tagcgaggct ggcgtttgtg cttgcactgg ccatagccgc ctcgtcaatt    60
gaggttgcgg agagcagaga ttttaatatc tttgctcagg gcagcttgcc tgatgcaacc   120
aagggatcgt ctggtctagc tgcaaccagt ggaaagttgt gtcagttatg cgagcagtac   180

```
tcatccgagg cgctcctcta tctcacacaa aacgagaccc agactgagat tcttagcatt    240
ctacaccatg aatgtgccag ccttgcccct ctcaaacagc agtgcatcac gctggttgac    300
tactacgtac ccctttcctt cttggaggtc tccatggtta ccccctgagaa gttctgcgag    360 tcgatgcatc tctgcaagaa ggggatgaag attagcctac ccacccggga gggtacttgt    420
ggtttgtgcc accatgttgt tgttgaaatt cttatcatgc ttaaagaccc caacatgcag    480
ctggaagtaa tcgacctact caccaaaaca tgcagcaagg cgcagaacta tgaacagtag    540
```

<210> SEQ ID NO 18
<211> LENGTH: 179
<212> TYPE: PRT
<213> ORGANISM: Zea mays

<400> SEQUENCE: 18

```
Met Cys Ser Val Ala Arg Leu Ala Phe Val Leu Ala Leu Ala Ile Ala
1               5                  10                  15

Ala Ser Ser Ile Glu Val Ala Glu Ser Arg Asp Phe Asn Ile Phe Ala
            20                  25                  30

Gln Gly Ser Leu Pro Asp Ala Thr Lys Gly Ser Ser Gly Leu Ala Ala
        35                  40                  45

Thr Ser Gly Lys Leu Cys Gln Leu Cys Glu Gln Tyr Ser Ser Glu Ala
    50                  55                  60

Leu Leu Tyr Leu Thr Gln Asn Glu Thr Gln Thr Glu Ile Leu Ser Ile
65                  70                  75                  80

Leu His His Glu Cys Ala Ser Leu Ala Pro Leu Lys Gln Gln Cys Ile
                85                  90                  95

Thr Leu Val Asp Tyr Tyr Val Pro Leu Phe Phe Leu Glu Val Ser Met
            100                 105                 110

Val Thr Pro Glu Lys Phe Cys Glu Ser Met His Leu Cys Lys Lys Gly
        115                 120                 125

Met Lys Ile Ser Leu Pro Thr Arg Glu Gly Thr Cys Gly Leu Cys His
    130                 135                 140

His Val Val Val Glu Ile Leu Ile Met Leu Lys Asp Pro Asn Met Gln
145                 150                 155                 160

Leu Glu Val Ile Asp Leu Leu Thr Lys Thr Cys Ser Lys Ala Gln Asn
                165                 170                 175

Tyr Glu Gln
```

<210> SEQ ID NO 19
<211> LENGTH: 1146
<212> TYPE: DNA
<213> ORGANISM: Zea mays

<400> SEQUENCE: 19

```
ggacactgac atggactgaa ggagtagaaa atccatccat tcccctcgcc aagccgccac     60
ggcctgactt tccctcccgc acacccgcga ccatacaggc aagtcaggca tacaccaaca    120 acgtcgtcg tgcacctcgc gcctcaggtc accccaccaa attcctcttg atacgccgaa    180
tttcttttgc taattctgct acctcctgtc gctaagccac catattcagt ctaacccctg    240
ctctgagctc acctgattgg cggctccgtt cggcctctgg gctgggtgt accgactacc    300 gagggctctt tcgaaatgtc aattgggtcg agtttggtgg gctacgtgaa gcatggatga    360
atttcccggc tggaagcggg aggcggcagc agcatccggg gccggagcac ctgtcgccga    420
tgacgccgct cccgctggcg cggtaggggt cggtctactc gctcacgttc gacgagttcc    480
```

-continued

| | |
|---|---|
| agagctcgct cggtggggcc accaaggact tcggatccat gaacatggac gagctcctcc | 540 |
| gcaacatctg gtcggcggag gagacacaca gcgtcacagc tgcggaccat gccgcgcggg | 600 |
| cgccgtacgt ccagtgccag ggctcgctca ccctcccctg cacgctcagc cagaagaccg | 660 |
| tcgacgaggt ctagcgtgac ctcgtgtgca acggtggagg accctccgac gaggctgtgg | 720 |
| cgccgcccca ccggcccaac ggcagccgac gctcgggag atcatgctgg aggagttcct | 780 |
| cgtccgcgcc ggcgtggtga gggaggacat gatggcggcg cgcccgtac caccagcgcc | 840 |
| gggttgccca ccacctcatc tgcaaccgcc aatgctgttt ccacatggca atgtgtttgc | 900 |
| tcccttagtg cctccgctcc aattcgggaa tgggtttgtg tcgggggctc tcagtcagca | 960 |
| gcagggaggt gttcttgagg ccccggcggt atcgccgcgg ccggtgacgg caagcgggtt | 1020 |
| cgggaagatg gaaggagacg acttgtcgca tctgtcgcca tcaccggtgt cgtacgtttt | 1080 |
| tttgtgctgg tttgagggga aggaagccac cagctgtgga aaggtggtt gagaggaggc | 1140 |
| aacgcc | 1146 |

<210> SEQ ID NO 20
<211> LENGTH: 357
<212> TYPE: PRT
<213> ORGANISM: Oryza glaberrima

<400> SEQUENCE: 20

```
Met Asp Phe Pro Gly Gly Ser Gly Arg Gln Gln Gln Leu Pro Pro Met
1               5                   10                  15

Thr Pro Leu Pro Leu Ala Arg Gln Gly Ser Val Tyr Ser Leu Thr Phe
            20                  25                  30

Asp Glu Phe Gln Ser Thr Leu Gly Gly Val Gly Lys Asp Phe Gly Ser
        35                  40                  45

Met Asn Met Asp Glu Leu Leu Arg Ser Ile Trp Thr Ala Glu Glu Ser
    50                  55                  60

His Ala Val Gly Ala Ala Thr Thr Thr Ala Thr Thr Ala Ser Val
65                  70                  75                  80

Ala Ala Ala Glu His Ala Ala Val Gly Ala Pro Pro Val Gln Arg Gln
                85                  90                  95

Gly Ser Leu Thr Leu Pro Arg Thr Leu Ser Gln Lys Thr Val Asp Glu
            100                 105                 110

Val Trp Arg Asp Met Met Cys Phe Gly Gly Gly Ala Ser Thr Ala
            115                 120                 125

Pro Ala Ala Ala Glu Pro Pro Pro Ala His Arg Gln Gln Thr Leu
    130                 135                 140

Gly Glu Ile Thr Leu Glu Glu Phe Leu Val Arg Ala Gly Val Val Arg
145                 150                 155                 160

Glu Asp Met Ser Val Pro Pro Val Pro Pro Ala Pro Thr Pro Thr Ala
                165                 170                 175

Ala Ala Val Pro Pro Pro Pro Pro Gln Gln Gln Thr Pro Met Leu
            180                 185                 190

Phe Gly Gln Ser Asn Val Phe Pro Pro Met Val Pro Pro Leu Ser Leu
        195                 200                 205

Gly Asn Gly Leu Val Ser Gly Ala Val Gly His Gly Gly Gly Ala
    210                 215                 220

Ala Ser Leu Val Ser Pro Val Arg Pro Val Ser Ser Asn Gly Phe Gly
225                 230                 235                 240

Lys Met Glu Gly Gly Asp Leu Ser Ser Leu Ser Pro Ser Pro Val Pro
                245                 250                 255
```

```
Tyr Val Phe Lys Gly Gly Leu Arg Gly Arg Lys Ala Pro Gly Ile Glu
            260                 265                 270

Lys Val Val Glu Arg Arg Gln Arg Met Ile Lys Asn Arg Glu Ser
        275                 280                 285

Ala Ala Arg Ser Arg Gln Arg Lys Gln Ala Tyr Met Met Glu Leu Glu
290                 295                 300

Ala Glu Val Ala Lys Leu Lys Glu Leu Asn Asp Glu Leu Gln Lys Lys
305                 310                 315                 320

Gln Asp Glu Met Leu Glu Gln Lys Asn Glu Val Leu Glu Arg Met
                325                 330                 335

Ser Arg Gln Val Gly Pro Thr Ala Lys Arg Ile Cys Leu Arg Arg Thr
            340                 345                 350

Leu Thr Gly Pro Trp
        355

<210> SEQ ID NO 21
<211> LENGTH: 1074
<212> TYPE: DNA
<213> ORGANISM: Oryza glaberrima

<400> SEQUENCE: 21
atggattttc cgggagggag cggggaggcag cagcagctgc cgccgatgac gccgctgccg      60
ttggcgaggc aggggtcggt gtactcgctc acgttcgacg agttccagag cacgctgggc     120
ggggtcggga aggacttcgg gtcgatgaac atggacgagc tcctccgcag catctggacg     180
gccgaggagt cgcacgccgt cggcgccgcc acgacgacga cggcgacgac ggcgtccgtg     240
gcggcggcgg agcacgcggc ggtggggcg ccgcccgttc agaggcaggg gtcgctgacc     300
ctcccccgca cgctcagcca gaagaccgtc gacgaggtct ggcgcgacat gatgtgcttc     360
ggtggcggcg gcgcctccac cgcgccggcc gccgcggagc cccgccgcc ggcgcaccgg     420 cagcagacgc tcggggagat cacgctggag gagttcctcg tgcgggccgg cgtggtgagg     480
gaggacatgt cggtcccgcc cgtcccgccg gcgccgactc ctacggcggc tgctgtacct     540
cccccgccgc cgccgcagca gcagacgccg atgttgttcg gtcagagcaa tgtgttccct     600
ccgatggtgc ctccgctctc gctgggaaat gggctggtct cgggagctgt cggacacggc     660
ggtggtggtg ccgcgtcgtt ggtttcgccg gtgaggccgg tctcgtccaa tggcttcggc     720
aagatggaag gcggggacct gtcgtcgctg tcgccatcgc cggtgccgta cgtttttcaaa     780 ggtgggctga ggggaaggaa ggcaccgggc atcgagaagg ttgtcgagag aagacagcgg     840
cggatgatca agaacaggga gtctgccgcg aggtcgcgcc agaggaaaca ggcatatatg     900
atggaattgg aagctgaggt agcaaaactt aaggagctga cgatgaact ccagaaaaag     960 caggatgaaa tgttggagca gcaaaagaat gaggttctag agagaatgag ccgacaagtt    1020
ggaccgacag caaagagaat ttgccttcgg aggactctga cgggtccatg gtga          1074

<210> SEQ ID NO 22
<211> LENGTH: 777
<212> TYPE: DNA
<213> ORGANISM: Zea mays

<400> SEQUENCE: 22
atgaatttcc cggctggaag cggggaggcgg cagcagcatc cggggccgga gcacctgtcg      60
ccgatgacgc cgctcccgct ggcgcggcag gggtcggtct actcgctcac gttcgacgag     120
ttccagagct cgctcggtgg ggccaccaag gacttcggat ccatgaacat ggacgagctc     180
```

```
ctccgcaaca tctggtcggc ggaggagaca cacagcgtca cagctgcgga ccatgccgcg    240
cgggcgccgt acgtccagtg ccagggctcg ctcaccctcc cctgcacgct cagccagaag    300
accgtcgacg aggtctggcg tgacctcgtg tgcaacggtg gaggaccctc cgacgaggct    360
gtggcggccg ccccaccggc ccaacggcag ccgacgctcg gggagatcat gctggaggag    420
ttcctcgtcc gcgccggcgt ggtgagggag gacatgatgg cggcggcgcc cgtaccacca    480
gcgccgggtt gcccaccacc tcatctgcaa ccgccaatgc tgtttccaca tggcaatgtg    540
tttgctccct tagtgcctcc gctccaattc gggaatgggt ttgtgtcggg ggctctcagt    600
cagcagcagg gaggtgttct tgaggccccg gcggtatcgc cgcggccggt gacggcaagc    660
gggttcggga agatggaagg agacgacttg tcgcatctgt cgccatcacc ggtgtcgtac    720 gttttttttgt gctggtttga ggggaaggaa gccaccagct gtggagaagg tggttga     777
```

<210> SEQ ID NO 23
<211> LENGTH: 258
<212> TYPE: PRT
<213> ORGANISM: Zea mays

<400> SEQUENCE: 23

```
Met Asn Phe Pro Ala Gly Ser Gly Arg Arg Gln Gln His Pro Gly Pro
1               5                   10                  15

Glu His Leu Ser Pro Met Thr Pro Leu Pro Leu Ala Arg Gln Gly Ser
            20                  25                  30

Val Tyr Ser Leu Thr Phe Asp Glu Phe Gln Ser Ser Leu Gly Gly Ala
        35                  40                  45

Thr Lys Asp Phe Gly Ser Met Asn Met Asp Glu Leu Leu Arg Asn Ile
    50                  55                  60

Trp Ser Ala Glu Glu Thr His Ser Val Thr Ala Ala Asp His Ala Ala
65                  70                  75                  80

Arg Ala Pro Tyr Val Gln Cys Gln Gly Ser Leu Thr Leu Pro Cys Thr
                85                  90                  95

Leu Ser Gln Lys Thr Val Asp Glu Val Trp Arg Asp Leu Val Cys Asn
            100                 105                 110

Gly Gly Gly Pro Ser Asp Glu Ala Val Ala Ala Ala Pro Pro Ala Gln
        115                 120                 125

Arg Gln Pro Thr Leu Gly Glu Ile Met Leu Glu Glu Phe Leu Val Arg
    130                 135                 140

Ala Gly Val Val Arg Glu Asp Met Met Ala Ala Ala Pro Val Pro Pro
145                 150                 155                 160

Ala Pro Gly Cys Pro Pro His Leu Gln Pro Met Leu Phe Pro
                165                 170                 175

His Gly Asn Val Phe Ala Pro Leu Val Pro Leu Gln Phe Gly Asn
            180                 185                 190

Gly Phe Val Ser Gly Ala Leu Ser Gln Gln Gln Gly Gly Val Leu Glu
        195                 200                 205

Ala Pro Ala Val Ser Pro Arg Pro Val Thr Ala Ser Gly Phe Gly Lys
    210                 215                 220

Met Glu Gly Asp Asp Leu Ser His Leu Ser Pro Ser Pro Val Ser Tyr
225                 230                 235                 240

Val Phe Leu Cys Trp Phe Glu Gly Lys Glu Ala Thr Ser Cys Gly Glu
                245                 250                 255

Gly Gly
```

<210> SEQ ID NO 24
<211> LENGTH: 1023
<212> TYPE: DNA
<213> ORGANISM: Zea mays

<400> SEQUENCE: 24

```
atgaatttcc cggctggaag cgggaggcgg cagcagcatc cggggccgga gcacctgtcg      60
ccgatgacgc cgctcccgct ggcgcggcag gggtcggtct actcgctcac gttcgacgag     120
ttccagagct cgctcggtgg ggccaccaag gacttcggat ctatgaacat ggacgagctc     180
ctccgcaaca tctggtcggc ggaggagaca cacagcgtca cagctgcgga ccatgccgcg     240
cgggcgccgt acgtccagtg ccagggctcg ctcaccctcc cctgcacgct cagccagaag     300
accgtcgacg aggtctggcg tgacctcgtg tgcaacggtg gaggaccctc cgacgaggct     360
gtggcggccg ccccaccggc caacggcag ccgacgctcg gggagatcat gctggaggag     420
ttcctcgtcc gcgccggcgt ggtgaggag acatgatgg cggcggcgcc cgtaccacca     480
gcgccgggtt gcccaccacc tcatctgcaa ccgccaatgc tgtttccaca tggcaatgtg     540
tttgctccct tagtgcctcc gctccaattc gggaatgggt ttgtgtcggg ggctctcagt     600
cagcagcagg gaggtgttct tgaggccccg gcggtatcgc cgcggccggt gacggcaagc     660
gggttcggga agatggaagg agacgacttg tcgcatctgt cgccatcacc ggtgtcgtac     720
gttttttttgt gctggtttga ggggaaggaa gccaccagct gtggacaagg tggtgagaga     780
agacagagga ggatgatcaa gaacagggag tctgccgcga ggtcgaggca gaggaaacag     840
gcatatatga tggaattgga agctgaggta gcaaagctca aggagctgaa cgacgagctc     900
cagaagaagc aggacgagat gctggagcag cagaagaacg aggtgctgga gaggatgtcc     960
aggcaggtgg gcccaaccgc caagaggatt tgcctgagga ggaccctgac cggcccatgg    1020
tga                                                                  1023
```

<210> SEQ ID NO 25
<211> LENGTH: 340
<212> TYPE: PRT
<213> ORGANISM: Zea mays

<400> SEQUENCE: 25

Met Asn Phe Pro Ala Gly Ser Gly Arg Arg Gln Gln His Pro Gly Pro
1               5                   10                  15

Glu His Leu Ser Pro Met Thr Pro Leu Pro Leu Ala Arg Gln Gly Ser
            20                  25                  30

Val Tyr Ser Leu Thr Phe Asp Glu Phe Gln Ser Ser Leu Gly Gly Ala
        35                  40                  45

Thr Lys Asp Phe Gly Ser Met Asn Met Asp Glu Leu Leu Arg Asn Ile
    50                  55                  60

Trp Ser Ala Glu Glu Thr His Ser Val Thr Ala Ala Asp His Ala Ala
65                  70                  75                  80

Arg Ala Pro Tyr Val Gln Cys Gln Gly Ser Leu Thr Leu Pro Cys Thr
                85                  90                  95

Leu Ser Gln Lys Thr Val Asp Glu Val Trp Arg Asp Leu Val Cys Asn
            100                 105                 110

Gly Gly Gly Pro Ser Asp Glu Ala Val Ala Ala Ala Pro Pro Ala Gln
        115                 120                 125

Arg Gln Pro Thr Leu Gly Glu Ile Met Leu Glu Glu Phe Leu Val Arg
    130                 135                 140

Ala Gly Val Val Arg Glu Asp Met Met Ala Ala Pro Val Pro Pro
145                 150                 155                 160

Ala Pro Gly Cys Pro Pro His Leu Gln Pro Pro Met Leu Phe Pro
            165                 170                 175

His Gly Asn Val Phe Ala Pro Leu Val Pro Pro Leu Gln Phe Gly Asn
        180                 185                 190

Gly Phe Val Ser Gly Ala Leu Ser Gln Gln Gln Gly Gly Val Leu Glu
        195                 200                 205

Ala Pro Ala Val Ser Pro Arg Pro Val Thr Ala Ser Gly Phe Gly Lys
    210                 215                 220

Met Glu Gly Asp Asp Leu Ser His Leu Ser Pro Ser Pro Val Ser Tyr
225                 230                 235                 240

Val Phe Leu Cys Trp Phe Glu Gly Lys Glu Ala Thr Ser Cys Gly Gln
            245                 250                 255

Gly Gly Glu Arg Arg Gln Arg Arg Met Ile Lys Asn Arg Glu Ser Ala
            260                 265                 270

Ala Arg Ser Arg Gln Arg Lys Gln Ala Tyr Met Met Glu Leu Glu Ala
    275                 280                 285

Glu Val Ala Lys Leu Lys Glu Leu Asn Asp Glu Leu Gln Lys Lys Gln
290                 295                 300

Asp Glu Met Leu Glu Gln Gln Lys Asn Glu Val Leu Glu Arg Met Ser
305                 310                 315                 320

Arg Gln Val Gly Pro Thr Ala Lys Arg Ile Cys Leu Arg Arg Thr Leu
            325                 330                 335

Thr Gly Pro Trp
            340

<210> SEQ ID NO 26
<211> LENGTH: 285
<212> TYPE: DNA
<213> ORGANISM: Zea mays

<400> SEQUENCE: 26
atgatgttct cctcctccct ctctgtggtg gagttttact tcctgcacag attccccctg      60
ccttttgctg gctacctcat cttcatttcc atattggctg gattctgggg ccagtgtttg     120
gttaggaaga tcgtgcatgt gctcaagaga gcatcgctta ttgtcttcat cctctcctct     180
gttatcttcg tcagtgctct tacgatgggt gtcgttggaa cccagaagag catttcgatg     240
atcaacaatc acgaatatat ggggttcctc aacttctgcg agtaa                    285

<210> SEQ ID NO 27
<211> LENGTH: 94
<212> TYPE: PRT
<213> ORGANISM: Zea mays

<400> SEQUENCE: 27

Met Met Phe Ser Ser Ser Leu Ser Val Val Glu Phe Tyr Phe Leu His
1               5                   10                  15

Arg Phe Pro Leu Pro Phe Ala Gly Tyr Leu Ile Phe Ile Ser Ile Leu
            20                  25                  30

Ala Gly Phe Trp Gly Gln Cys Leu Val Arg Lys Ile Val His Val Leu
        35                  40                  45

Lys Arg Ala Ser Leu Ile Val Phe Ile Leu Ser Ser Val Ile Phe Val
    50                  55                  60

Ser Ala Leu Thr Met Gly Val Val Gly Thr Gln Lys Ser Ile Ser Met
65                  70                  75                  80

Ile Asn Asn His Glu Tyr Met Gly Phe Leu Asn Phe Cys Glu
            85                  90

<210> SEQ ID NO 28
<211> LENGTH: 377
<212> TYPE: DNA
<213> ORGANISM: Zea mays

<400> SEQUENCE: 28

```
atggcgtctg cagtgaccag cagcgacaag gagcaggccg tccctaccat cgacgctgac      60
gaagcgcacg cgctgctgag ctccggccat ggctacgtgg atgtcaggat gcgggggggac    120
ttccacaagg cgcatgcgcc cggtgctcgg aacgttccct actacctgtc cgtcacgccg    180
caagggaagg agaagaaccc acactttgta gaggaagtgg ctgccttctg tgggaaggat    240
gatgtcttca ttgtgggttg caacacgggg aacagatcca ggttcgcgac ggcagacctt    300
ctgaacgcgg ggttcaagaa cgtgaggaac ctgcaaggtg gttaccgctc ctttcagcag    360
cgagctcaac agcagta                                                     377
```

<210> SEQ ID NO 29
<211> LENGTH: 125
<212> TYPE: PRT
<213> ORGANISM: Zea mays

<400> SEQUENCE: 29

Met Ala Ser Ala Val Thr Ser Ser Asp Lys Glu Gln Ala Val Pro Thr
1               5                   10                  15

Ile Asp Ala Asp Glu Ala His Ala Leu Leu Ser Ser Gly His Gly Tyr
            20                  25                  30

Val Asp Val Arg Met Arg Gly Asp Phe His Lys Ala His Ala Pro Gly
        35                  40                  45

Ala Arg Asn Val Pro Tyr Tyr Leu Ser Val Thr Pro Gln Gly Lys Glu
    50                  55                  60

Lys Asn Pro His Phe Val Glu Glu Val Ala Ala Phe Cys Gly Lys Asp
65                  70                  75                  80

Asp Val Phe Ile Val Gly Cys Asn Thr Gly Asn Arg Ser Arg Phe Ala
                85                  90                  95

Thr Ala Asp Leu Leu Asn Ala Gly Phe Lys Asn Val Arg Asn Leu Gln
            100                 105                 110

Gly Gly Tyr Arg Ser Phe Gln Gln Arg Ala Gln Gln Gln
        115                 120                 125

<210> SEQ ID NO 30
<211> LENGTH: 411
<212> TYPE: DNA
<213> ORGANISM: Zea mays

<400> SEQUENCE: 30

```
atggaggcga agaagaagcc gtcggccccc gccgccgtcg agccgcgcc gccgccgccg      60
ggtaacgggt acttcagcac cgtcttctcc gcgccgactg cgggaagcgc aagtgacgca    120
aagcatgcgg acttgtacac gatgctgaac aagcagagct ccagagggca gaatggcaga    180
gatggcaaat cccacagccg ccctacttac aaggatggca acatgctca tccaaatgag     240
ccatcagaat ctccttactt tggctcatcc gtgcattacg gtggtcggga gttctacagc    300
agcgttttac ggaagcaacc agccaatgaa ccccatacga attacaaggg ggacaacccg    360
gatggctctg ctaccagagg tgattggtgg caaggttcac tttattactg a              411
```

<210> SEQ ID NO 31
<211> LENGTH: 136
<212> TYPE: PRT
<213> ORGANISM: Zea mays

<400> SEQUENCE: 31

Met Glu Ala Lys Lys Pro Ser Ala Pro Ala Ala Val Gly Ala Ala
1               5                   10                  15

Pro Pro Pro Gly Asn Gly Tyr Phe Ser Thr Val Phe Ser Ala Pro
            20                  25                  30

Thr Ala Gly Ser Ala Ser Asp Ala Lys His Ala Asp Leu Tyr Thr Met
        35                  40                  45

Leu Asn Lys Gln Ser Ser Arg Gly Gln Asn Gly Arg Asp Gly Lys Ser
    50                  55                  60

His Ser Arg Pro Thr Tyr Lys Asp Gly Lys His Ala His Pro Asn Glu
65                  70                  75                  80

Pro Ser Glu Ser Pro Tyr Phe Gly Ser Ser Val His Tyr Gly Gly Arg
                85                  90                  95

Glu Phe Tyr Ser Ser Val Leu Arg Lys Gln Pro Ala Asn Glu Pro His
            100                 105                 110

Thr Asp Tyr Lys Gly Asp Asn Pro Asp Gly Ser Ala Thr Arg Gly Asp
        115                 120                 125

Trp Trp Gln Gly Ser Leu Tyr Tyr
    130                 135

<210> SEQ ID NO 32
<211> LENGTH: 162
<212> TYPE: DNA
<213> ORGANISM: Zea mays

<400> SEQUENCE: 32
atggaccgga acctgagcgg gtttctgatc gggtgcctgg gcgccgccgt gacgctgctg      60
gcgtaccagc agacggtggt gaccagcacg cagagcgtcg cggcgggctt cgtcgtcatc     120
ctcttcgccc tcttcgtcaa ggaaggattc atttccctct ga                        162

<210> SEQ ID NO 33
<211> LENGTH: 53
<212> TYPE: PRT
<213> ORGANISM: Zea mays

<400> SEQUENCE: 33

Met Asp Arg Asn Leu Ser Gly Phe Leu Ile Gly Cys Leu Gly Ala Ala
1               5                   10                  15

Val Thr Leu Leu Ala Tyr Gln Gln Thr Val Val Thr Ser Thr Gln Ser
            20                  25                  30

Val Ala Ala Gly Phe Val Val Ile Leu Phe Ala Leu Phe Val Lys Glu
        35                  40                  45

Gly Phe Ile Ser Leu
    50

<210> SEQ ID NO 34
<211> LENGTH: 669
<212> TYPE: DNA
<213> ORGANISM: Zea mays

<400> SEQUENCE: 34
atggcatgcg tcagcaccct tccagagctgc cccattgcca gaagagcaaa gatcaacacc     60

```
aggtccaggg gcagcagcag tagcgtggcg aagggggtcac caccaccagc cttccagttc    120
cagtgcaggg cgtcgacttt cgcggcggac accagcctcc ggctcgagct ggacgagaac    180
cccgaggcga tcatctcggg ggcgtggccc gggaactgct ccctcctcag ctacgacgac    240
ctccgcgcct acctcgagtc gcaggagacg gcggcccagg cagacgatca gcgcggcgtg    300
gcgctcctga gcgagaccat gtccacaccc gtgctggtgg ccacagcaga ccagaccctg    360
gaggacgtcg agtgccactt cgaggccgtg tcgggcttc cggtcgtcga cagcggcctc    420
agatgcgtcg gggtgatcgt caagaacgac cgggcaagag cctctcatgg gtccaagacg    480
aagatatcgg aagtgatgac atctccagct atcacactat cgtctgacaa aaccgtgatg    540
gatgctgctg ttctcatgct caagaagaag atccacagat accagttgt aaaccaggac    600 gaaaaagtaa taggtatagt tacccgcgct gatgttcttc gcgtgttgga aggcatgttg    660
aagatttag                                                          669
```

<210> SEQ ID NO 35
<211> LENGTH: 222
<212> TYPE: PRT
<213> ORGANISM: Zea mays

<400> SEQUENCE: 35

```
Met Ala Cys Val Ser Thr Phe Gln Ser Cys Pro Ile Ala Arg Arg Ala
1               5                   10                  15

Lys Ile Asn Thr Arg Ser Arg Gly Ser Ser Ser Val Ala Lys Gly
            20                  25                  30

Ser Pro Pro Ala Phe Gln Phe Gln Cys Arg Ala Ser Thr Phe Ala
        35                  40                  45

Ala Asp Thr Ser Leu Arg Leu Glu Leu Asp Glu Asn Pro Glu Ala Ile
    50                  55                  60

Ile Ser Gly Ala Trp Pro Gly Asn Cys Ser Leu Leu Ser Tyr Asp Asp
65                  70                  75                  80

Leu Arg Ala Tyr Leu Glu Ser Gln Glu Thr Ala Ala Gln Ala Asp Asp
                85                  90                  95

Gln Arg Gly Val Ala Leu Leu Ser Glu Thr Met Ser Thr Pro Val Leu
            100                 105                 110

Val Ala Thr Ala Asp Gln Thr Leu Glu Asp Val Glu Cys His Phe Glu
        115                 120                 125

Ala Val Ser Gly Leu Pro Val Val Asp Ser Gly Leu Arg Cys Val Gly
    130                 135                 140

Val Ile Val Lys Asn Asp Arg Ala Arg Ala Ser His Gly Ser Lys Thr
145                 150                 155                 160

Lys Ile Ser Glu Val Met Thr Ser Pro Ala Ile Thr Leu Ser Ser Asp
                165                 170                 175

Lys Thr Val Met Asp Ala Ala Val Leu Met Leu Lys Lys Lys Ile His
            180                 185                 190

Arg Leu Pro Val Val Asn Gln Asp Glu Lys Val Ile Gly Ile Val Thr
        195                 200                 205
```

Arg Ala Asp Val Leu Arg Val Leu Glu Gly Met Leu Lys Ile
    210             215                 220

<210> SEQ ID NO 36
<211> LENGTH: 537
<212> TYPE: DNA
<213> ORGANISM: Zea mays

<400> SEQUENCE: 36
atgggcgacc tctctgtcgg ccacagccgc cgctggtgcg ccgtttcgc ggccgtcctt      60 tgcctgtgcg cggccttctg caagccagat gaactcccga tggatccact gccgaacttg     120
ccgccgacga gtcgctgca gtgcttcgag acgaacagg tgtacagctg ctgcgagggc      180
gcgtacaggc taaacccatc gggaatcatc gccgttcccg tcggcgcggt ggactactac     240
tgcggcggcg cgtgcgtggt ggagacggag gacgtgctca actgcgtggc cagcgccctg     300
gacggcttcg ccttctacaa cggggcctcc gtggaggacg tgcgctacgc actcaggcgg     360
ggctgcagcc acaccgccag aagaggcgac ttcaacgatt tggagccgca tctgggcgac     420
taccctgaca tctatggcga cgatgatgag cacagctttg gcagcaaggt tgttgcagct     480
cctctgaggt tgctcgcgtt tcttggcggt gcggggctgt tcttcctggg cccttga        537

<210> SEQ ID NO 37
<211> LENGTH: 178
<212> TYPE: PRT
<213> ORGANISM: Zea mays

<400> SEQUENCE: 37

Met Gly Asp Leu Ser Val Gly His Ser Arg Arg Trp Cys Gly Arg Phe
1               5                   10                  15

Ala Ala Val Leu Cys Leu Cys Ala Ala Phe Cys Lys Pro Asp Glu Leu
            20                  25                  30

Pro Met Asp Pro Leu Pro Asn Leu Pro Pro Thr Arg Ser Leu Gln Cys
        35                  40                  45

Phe Glu Asp Glu Gln Val Tyr Ser Cys Cys Glu Gly Ala Tyr Arg Leu
    50                  55                  60

Asn Pro Ser Gly Ile Ile Ala Val Pro Val Gly Ala Val Asp Tyr Tyr
65                  70                  75                  80

Cys Gly Gly Ala Cys Val Val Glu Thr Glu Asp Val Leu Asn Cys Val
                85                  90                  95

Ala Ser Ala Leu Asp Gly Phe Ala Phe Tyr Asn Gly Ala Ser Val Glu
            100                 105                 110

Asp Val Arg Tyr Ala Leu Arg Arg Gly Cys Ser His Thr Ala Arg Arg
        115                 120                 125

Gly Asp Phe Asn Asp Leu Glu Pro His Leu Gly Asp Tyr Pro Asp Ile
    130                 135                 140

Tyr Gly Asp Asp Asp Glu His Ser Phe Gly Ser Lys Val Val Ala Ala
145                 150                 155                 160

Pro Leu Arg Leu Leu Ala Phe Leu Gly Gly Ala Gly Leu Phe Phe Leu
                165                 170                 175

Gly Pro

<210> SEQ ID NO 38
<211> LENGTH: 822
<212> TYPE: DNA
<213> ORGANISM: Zea mays

<400> SEQUENCE: 38

```
atggattcgg aggcggtgca gcacggcctt ctccctctgt ctgcctgtcc tcctaccgcc    60
aacagctgcg cgcattacag ccgtgggtgc agcgtcgtgg cgccctgctg cggccaggcc   120
ttcggctgcc gccattgcca acgacgcc aagaactcgc tggaggtcga cccgcgcgac    180
cggcacgaga tcccccgcca cgaaataaag aaggtgatct gttctctctg ctccaaggaa   240
caggacgtgc aacagaactg ctccagctgt ggggcctgca tgggcaagta cttctgtaaa   300
gtatgcaagt tcttcgatga tgatgcctca aagggccagt accactgtga cggatgtgga   360
atatgtagaa ccggcggcgt ggagaacttt ttccactgtg ataaatgtgg gtgttgctac   420
agcaatgtct tgaaggattc ccaccactgc gtcgaaagag caatgcatca aactgccccc   480
gtctgctttg agtatctgtt cgactccacg aaggacatca gcgtgctgca atgtgggcat   540
accatccatt tggagtgcat gaacgagatg agagcacacc atcacttctc atgcccagtg   600
tgctcgaggt ccgcctgcga catgtcggcc acatggcgga agctcgacga ggaggtcgcg   660
gccacgccga tgcctgacat ctaccagaag cacatggtgt ggatcctgtg caacgactgc   720
agcgcgacct cgagcgtgcg gttccacgtg ctggggcaca gtgccccgc gtgcagctcg   780
tacaacaccc gggagacgag ggctgcgtgc cccaggatct ga                     822
```

<210> SEQ ID NO 39
<211> LENGTH: 273
<212> TYPE: PRT
<213> ORGANISM: Zea mays

<400> SEQUENCE: 39

```
Met Asp Ser Glu Ala Val Gln His Gly Leu Leu Pro Leu Ser Ala Cys
1               5                   10                  15
Pro Pro Thr Ala Asn Ser Cys Ala His Tyr Ser Arg Gly Cys Ser Val
            20                  25                  30
Val Ala Pro Cys Cys Gly Gln Ala Phe Gly Cys Arg His Cys His Asn
        35                  40                  45
Asp Ala Lys Asn Ser Leu Glu Val Asp Pro Arg Asp Arg His Glu Ile
    50                  55                  60
Pro Arg His Glu Ile Lys Lys Val Ile Cys Ser Leu Cys Ser Lys Glu
65                  70                  75                  80
Gln Asp Val Gln Gln Asn Cys Ser Ser Cys Gly Ala Cys Met Gly Lys
                85                  90                  95
Tyr Phe Cys Lys Val Cys Lys Phe Phe Asp Asp Ala Ser Lys Gly
            100                 105                 110
Gln Tyr His Cys Asp Gly Cys Gly Ile Cys Arg Thr Gly Gly Val Glu
        115                 120                 125
Asn Phe Phe His Cys Asp Lys Cys Gly Cys Cys Tyr Ser Asn Val Leu
    130                 135                 140
Lys Asp Ser His His Cys Val Glu Arg Ala Met His His Asn Cys Pro
145                 150                 155                 160
Val Cys Phe Glu Tyr Leu Phe Asp Ser Thr Lys Asp Ile Ser Val Leu
                165                 170                 175
Gln Cys Gly His Thr Ile His Leu Glu Cys Met Asn Glu Met Arg Ala
            180                 185                 190
His His His Phe Ser Cys Pro Val Cys Ser Arg Ser Ala Cys Asp Met
        195                 200                 205
Ser Ala Thr Trp Arg Lys Leu Asp Glu Glu Val Ala Ala Thr Pro Met
    210                 215                 220
```

-continued

```
Pro Asp Ile Tyr Gln Lys His Met Val Trp Ile Leu Cys Asn Asp Cys
225                 230                 235                 240

Ser Ala Thr Ser Ser Val Arg Phe His Val Leu Gly His Lys Cys Pro
                245                 250                 255

Ala Cys Ser Ser Tyr Asn Thr Arg Glu Thr Arg Ala Ala Cys Pro Arg
                260                 265                 270

Ile
```